(12) United States Patent
Farrelly et al.

(10) Patent No.: US 11,903,785 B2
(45) Date of Patent: Feb. 20, 2024

(54) SHADE MATCHING AND LOCALIZED LABORATORY AESTHETICS FOR RESTORATIVE DENTISTRY

(71) Applicant: Porchview, LLC, Cary, NC (US)

(72) Inventors: Megan Farrelly, Raleigh, NC (US); Eugene Farrelly, Cary, NC (US)

(*) Notice: Subject to any disclaimer, the term of this patent is extended or adjusted under 35 U.S.C. 154(b) by 331 days.

(21) Appl. No.: 16/907,083

(22) Filed: Jun. 19, 2020

(65) Prior Publication Data
US 2020/0397534 A1 Dec. 24, 2020

Related U.S. Application Data

(60) Provisional application No. 62/865,193, filed on Jun. 22, 2019.

(51) Int. Cl.
| | | |
|---|---|---|
| *G06Q 10/087* | (2023.01) | |
| *G16H 50/70* | (2018.01) | |
| *G16H 40/20* | (2018.01) | |
| *G16H 50/20* | (2018.01) | |
| *A61C 5/77* | (2017.01) | |
| *A61C 13/08* | (2006.01) | |
| *A61C 13/00* | (2006.01) | |
| *A61C 19/10* | (2006.01) | |

(52) U.S. Cl.
CPC ........... *A61C 5/77* (2017.02); *A61C 13/0004* (2013.01); *A61C 13/082* (2013.01); *G06Q 10/087* (2013.01); *G16H 40/20* (2018.01); *G16H 50/20* (2018.01); *G16H 50/70* (2018.01); *A61C 19/10* (2013.01)

(58) Field of Classification Search
CPC ..... G06T 19/00–20; G06T 2207/30036; G06T 7/0012; A61B 5/4547; A61B 5/1032; G01J 3/508; G01J 3/45; G09B 19/0023; G16H 40/20; G16H 50/70; G16H 50/20; G06Q 10/087
See application file for complete search history.

(56) References Cited

U.S. PATENT DOCUMENTS

| | | | |
|---|---|---|---|
| 2002/0081547 A1* | 6/2002 | Kerschbaumer | A61C 19/10 433/26 |
| 2012/0231421 A1* | 9/2012 | Boerjes | A61C 9/0046 433/223 |
| 2013/0066750 A1* | 3/2013 | Siddique | G06Q 40/12 705/27.2 |
| 2013/0244197 A1* | 9/2013 | Tjioe | G01J 3/0264 433/29 |
| 2014/0157579 A1* | 6/2014 | Chhabra | B33Y 50/00 705/26.4 |
| 2019/0125503 A1* | 5/2019 | Krolikowski | B33Y 70/00 |

OTHER PUBLICATIONS

PCT Internat. Search Rep., dated Jun. 19, 2020, PCT/US20/38827.

* cited by examiner

*Primary Examiner* — Jay M. Patel
(74) *Attorney, Agent, or Firm* — ROARK IP

(57) ABSTRACT

Embodiments of the present disclosure create an "exchange" where dentists who invest in on-site restoration technologies can share their restoration design, restoration supplies, characterization knowledge, and idle milling time with local dentists. Suppliers can further offer quality control by double checking designs and selections. The platform of shade measurements, block selections, and characterization recommendations further serves as a resource to the dental community at large for improving shade matching in dentistry restorations.

16 Claims, 23 Drawing Sheets

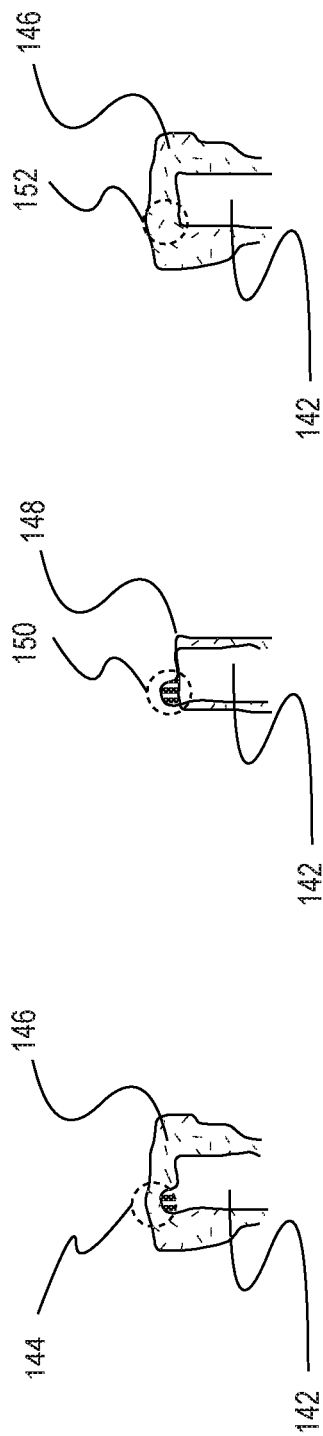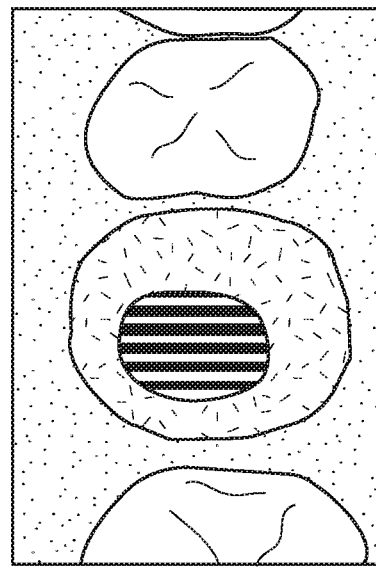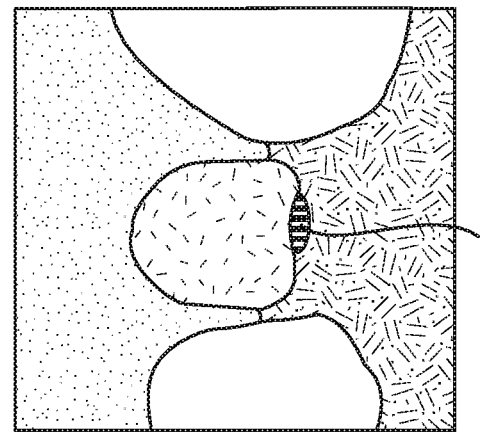

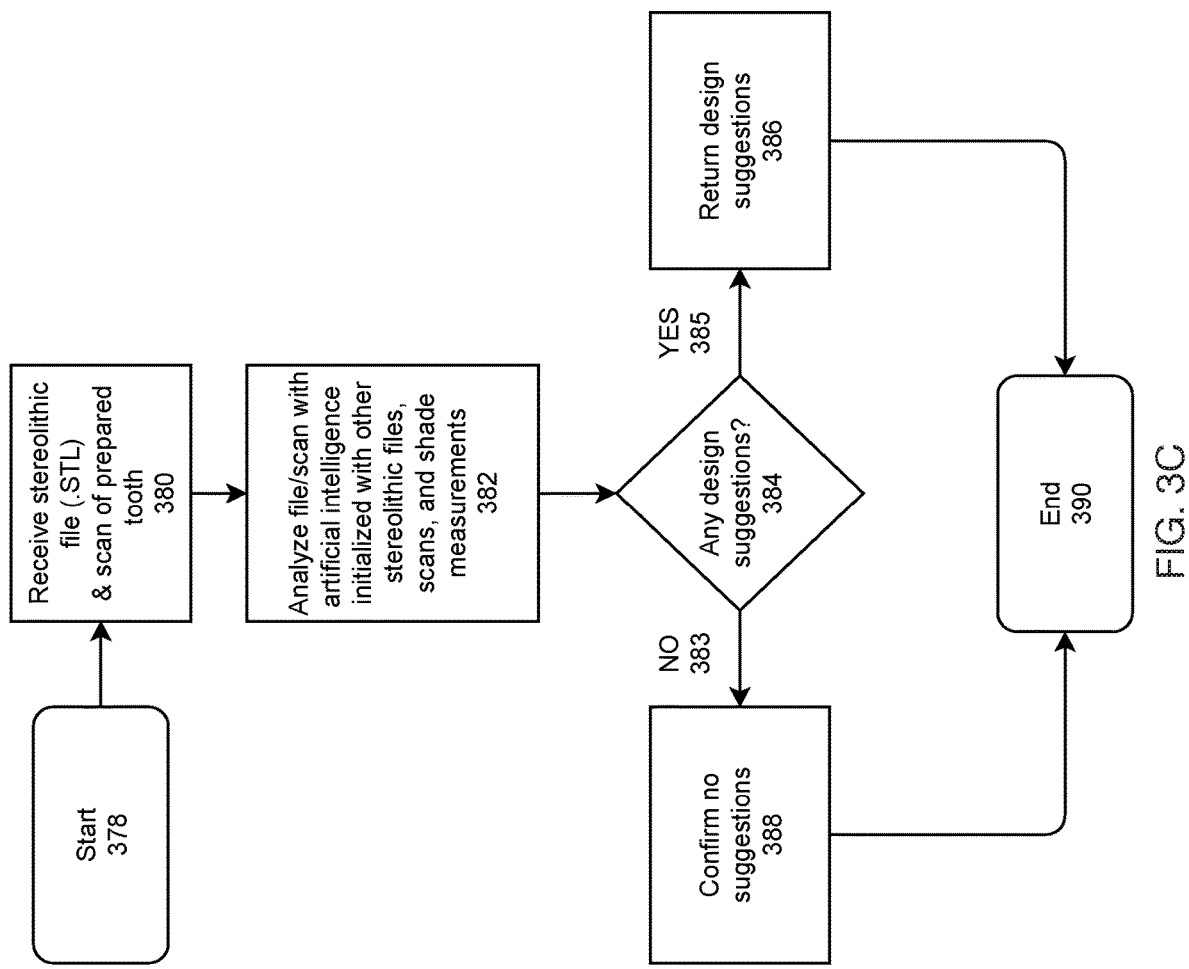

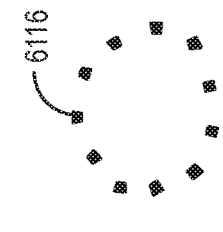 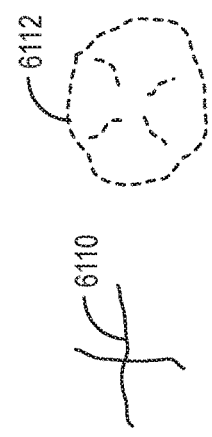 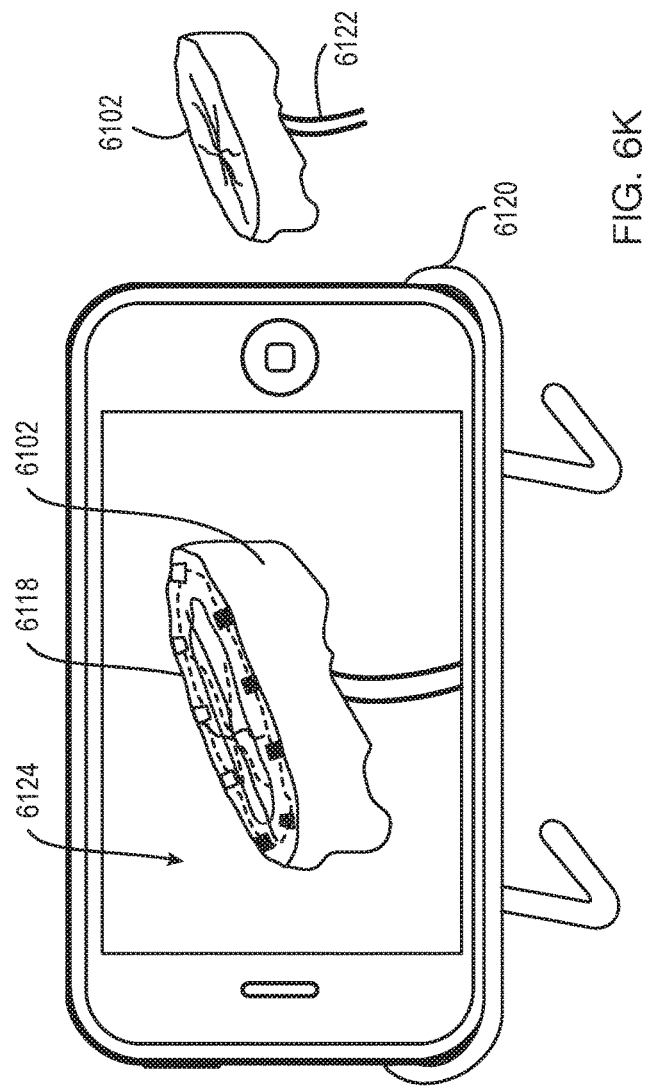
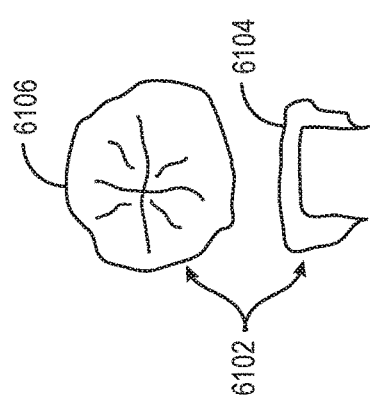 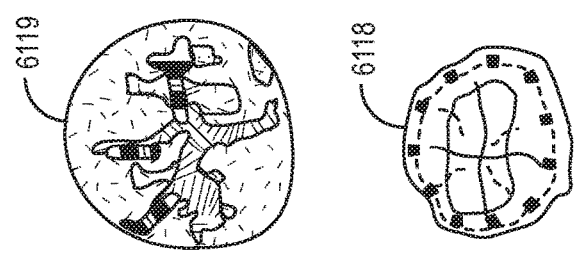

SHADE MATCHING AND LOCALIZED LABORATORY AESTHETICS FOR RESTORATIVE DENTISTRY

CROSS REFERENCE TO RELATED APPLICATION

This application claims the benefit of U.S. Provisional Patent Applications No. 62/865,193 filed Jun. 22, 2019, the disclosures of which are incorporated herein by reference in their entirety.

TECHNICAL FIELD

The present disclosure relates to shade matching and localized laboratory aesthetics for restorative dentistry.

BACKGROUND

Recent years have seen incredible advancements in computer aided design (CAD)/computer aided manufacturing (CAM) dentistry. Software, products, and solutions from such companies as Dentsply Sirona, iTero, MEDIT, 3shape, Dental Wings, Carestream, Planmeca, Zimmer Biomet, Danaher and Align have made the promise of same-day dental restorations (such as crowns, inlays, onlays, etc.) possible.

Advancements have also made possible sophisticated shade matching techniques and devices available to dentists to help better match the color of restorations to the natural color of patients' teeth. Spectrophotometer solutions such as those from such companies as Vita, Vident, Crystaleye, and Olympus allow the dentist to accurately record tooth chroma, value, and hue (collectively referred to simply as shade). Chroma refers to the intensity or saturation (which can be thought of as strength or dominance). Hue is the color tone (red, purple, blue). Value refers to the lightness or darkness of only one of the colors that may exist by itself.

SUMMARY OF THE DISCLOSURE

Aspects of the disclosure include a shade matching server device comprising: one or more processors; one or more communications interfaces; memory containing instructions executable by the one or more processors with the one or more communications interfaces whereby the server device is operable to: receive a stereo lithic file and a shade measurement for a design of a restoration for a target patient from a requesting computing device: receive a geographic area designation from the requesting computing device; receive inventory information from a plurality of supplying computing devices; generate one or more material recommendations for the restoration for the target patient based on inventory information from a plurality of supplying computing devices that match the geographic area designation; receive stereo lithic files and shade measurements for restorations for other patients from supplying computing devices; invoke a machine learning process with the stereo lithic file and shade measurement for the restoration for the target patient; generate one or more characterization recommendations for the restoration for the target patient based on machine learning and statistical models; and send the one or more material recommendations and the one or more characterization recommendations for the restoration for the target patient to the requesting computing device. Applying the machine learning process may involve applying a translation process to the stereo lithic file for the restoration of the target patient and the stereo lithic files for the restorations for other patients and/or applying a genetic process to the stereo lithic file for the restoration of the target patient and the stereo lithic files for the restorations for other patients. The one or more characterization recommendations may include one or more staining or glazing recommendations, spatial information, or information for using the spatial information of the one or more characterization recommendations in an augmented reality application. The server device is further operable to: rank order the one or more material recommendations or rank order the one or more characterization recommendations. Wherein the one or more material recommendations are rank ordered by one of the methods in the group comprising of: the shade of the material that best matches the shade measurement, the cost of the material, the availability of the material, the estimated target delivery time of the material, and the estimated target delivery time of a restoration created from the material. The geographic area designation may be one of the group comprising: a physical address, latitude and longitudinal coordinates, what3words, zip code, point and a radius, and an arbitrary polygon. The shade measurement may include individual measurements for chroma, hue, and value. Generating the one or more material recommendations may include matching the closest values of the individual measurements of chroma, hue, and value for both the shade measurement and the material recommendation. The shade measurement may include an aggregate measure of chroma, hue, and value. Generating the one or more material recommendations may include matching the closest aggregate measure of chroma, hue, and value for both the shade measurement and the material recommendation. The one or more materials recommendations may be selected from the group of materials comprising: feldspathic porcelain, ceramic resin hybrid, leucite-reinforced porcelain, lithium disilicate, nano ceramic/resin, composite resin, and zirconia reinforced lithium silicate. The server device is further operable to: detect a minimum depth error based on the design file and the material recommendation selection; and request a reduction coping, request the manufacture of a restoration based on the design file, receive information indicating the completion of the manufacture of the restoration, receive information indicating the completion of the reduction coping, initiate a delivery request with a delivery service which may include receiving delivery information to the requesting computing device and/or sending delivery information to a delivery service. The server device is further operable to: determine if the design file contains identifying information which may be one of the group comprising: information identifying a dentist, a dental office, and a patient. The server device is further operable to: remove identifying information from the design file.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 1A illustrates a dental manufacturing system and method 100.

FIGS. 1B-1D illustrate dental prosthetic items (e.g., exemplary blocks) associated with the dental manufacturing system and method 100. There may be an array of materials in any given blocks. And there are blocks of different materials (not shown), for example Express CAD LT A2/I12, Katana Zirconia Block 12z/STMCA2, and many others.

FIG. 3C illustrates a flow chart associated with the machine learning process of the system of shade matching and localized laboratory aesthetics for restorative design in dentistry.

FIG. 4A illustrates an exemplary user interface under one embodiment of the present disclosure for defining the designated geographical area.

FIG. 5 illustrates an exemplary user interface under one embodiment of the present disclosure for ranking, selecting, and ordering inventory.

FIGS. 6E-6K illustrates an example of augmented reality applied to the staining and glazing step of the system of shade matching and localized laboratory aesthetics for restorative design in dentistry.

DETAILED DESCRIPTION

Figure 1A:
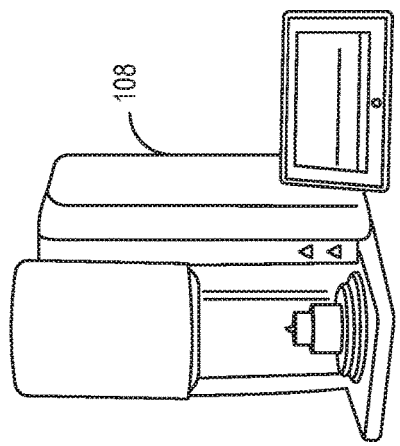
FIG. 1E illustrates an exemplary spectrophotometer device. Specific examples (not shown) include the Crystal Eye spectrophotometer which is good for efficacy of vital tooth shading by using numerical color data.
FIGS. 1F-1J illustrates reduction coping.
FIG. 1K illustrates a perspective schematic view 106b of the manufacturing component 106a to illustrate the high level components therein.
Figure 1A:
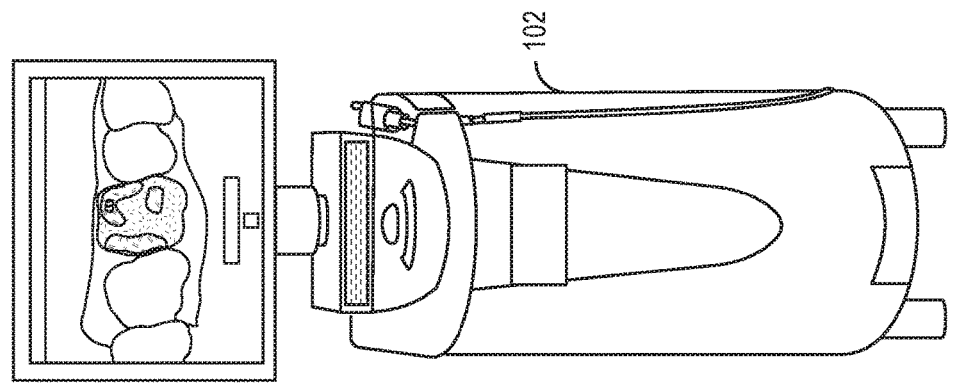
Figure 1A:
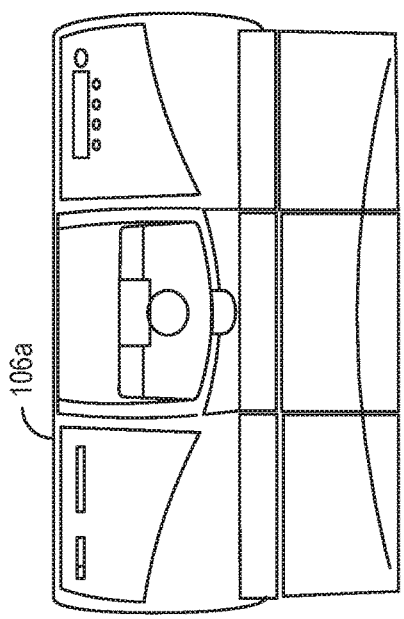
Figure 1A:
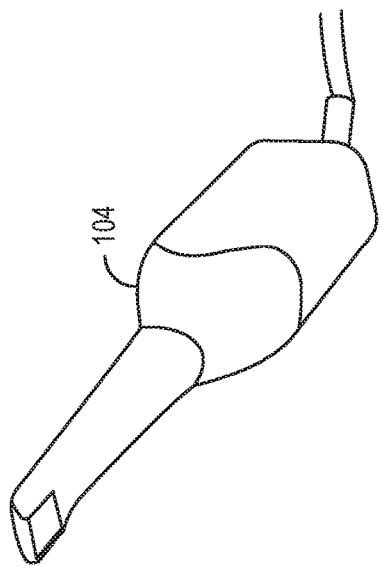

The present disclosure is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Throughout this specification, like reference numbers signify the same elements throughout the description of the figures.

When elements are referred to as being "connected" or "coupled," the elements can be directly connected or coupled together or one or more intervening elements may also be present. In contrast, when elements are referred to as being "directly connected" or "directly coupled," there are no intervening elements present.

As referred to herein, the terms "user device" and "mobile device" should be broadly construed. They can include any type of mobile device, for example, a smart phone, a cell phone, a pager, a personal digital assistant (PDA, e.g., with general packet radio service (GPRS) network interface controller (NIC)), a mobile computer with a cellular radio, or the like. A typical mobile device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol (IP) and the wireless application protocol (WAP). This allows users to access information via wireless devices, such as smart phones, mobile phones, pagers, two-way radios, communicators, and the like. Wireless data access is supported by many wireless networks, including, but not limited to, cellular digital packet data (CDPD), code-division multiple access (CDMA), global system for mobile communications (GSM), personal digital cellular (PDC), personal handy-phone system (PHS), time-division multiple access (TDMA), FLEX communications protocol, ReFLEX communications protocol, integrated digital enhanced network (iDEN), terrestrial trunked radio (TETRA), digital enhanced cordless telecommunications (DECT), DataTAC wireless data network technology, Mobitex wireless packet-switched data network, Enhanced Data rates for GSM Evolution (EDGE) and other 2G, 3G, 4G and LTE, and 5G technologies, and it operates with many handheld device operating systems, such as PalmOS, EPOC mobile operating system, Windows Embedded Compact, OS/9 operating systems, JavaOS operating system, iOS mobile operating system and Android® mobile operating system. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition, a mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on a mobile device, the examples may similarly be implemented on any suitable user device 270.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be for example, but not limited to, an electronic, magnetic, optical, electromagnetic, infrared, or semiconductor system, apparatus, device, or propagation medium. By way of example, and not limitation, computer-readable media may comprise computer storage media and communication media.

Computer storage media includes volatile and non-volatile, removable and non-removable media implemented in any method or technology for storage of information such as computer-readable instructions, data structures, program modules, or other data. Computer storage media includes, but is not limited to, random access memory (RAM), read-only memory (ROM), electrically erasable programmable read-only memory (EEPROM), flash memory or other memory technology, compact disc (CD)-read-only memory (ROM), digital versatile disks (DVD) or other optical storage, magnetic cassettes, magnetic tape, magnetic disk storage or other magnetic storage devices, solid state devices, or any other medium which can be used to store the desired information and may be accessed by an instruction execution system. Note that the computer-usable or computer-readable medium can be paper or other suitable medium upon which the program is printed, as the program can be electronically captured via, for instance, optical scanning of the paper or other suitable medium, then compiled, interpreted, or otherwise processed in a suitable manner, if necessary, and then stored in a computer memory. In some embodiments, computer storage media could include cloud-based storage such as that offered by Amazon Simple Storage Service (S3) or Amazon Elastic Block Storage (EBS) and the like.

Communication media typically embodies computer-readable instructions, data structures, program modules or other data in a modulated data signal such as a carrier wave or other transport mechanism and includes any information delivery media. The term "modulated data signal" can be defined as a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above-mentioned should also be included within the scope of computer-readable media.

When the subject matter is embodied in the general context of computer-executable instructions, the embodiment may comprise program modules, executed by one or more systems, computers, or other devices. Generally, program modules include routines, programs, objects, components, data structures, and the like, that perform particular tasks or implement particular abstract data types. Typically, the functionality of the program modules may be combined or distributed as desired in various embodiments.

Operating environments in which embodiments of the present disclosure may be implemented are also well-known. In a representative embodiment, a user device 270 (shown in FIG. 2A), such as a mobile device, is connectable to a transmission functionality that varies depending on implementation. Thus, for example, where the operating environment is a wide area wireless network (e.g., a 2.5G network, a 3G network, a 4G network, or a 5G network, etc.), the transmission functionality comprises one or more components such as a mobile switching center (MSC) (an enhanced integrated services digital network (ISDN) switch that is responsible for call handling of mobile subscribers), a visitor location register (VLR) (an intelligent database that stores on a temporary basis data required to handle calls set up or received by mobile devices registered with the VLR), a home location register (HLR) (an intelligent database responsible for management of each subscriber's records), one or more base stations (which provide radio coverage with a cell), a base station controller (BSC) (a switch that acts as a local concentrator of traffic and provides local switching to effect handover between base stations), and a packet control unit (PCU) (a device that separates data traffic coming from a mobile device). The HLR also controls certain services associated with incoming calls. Of course, the present disclosure may be implemented in other and next-generation mobile networks and devices as well. The mobile device is the physical equipment used by the end user, usually a subscriber to the wireless network. Typically, a mobile device is a 2.5G-compliant device, 3G-compliant device, 4G-compliant device, or 5G-compliant device that includes a subscriber identity module (SIM), which is a smart card that carries subscriber-specific information, mobile equipment (e.g., radio and associated signal processing devices), a user interface (or a man-machine interface (MMI)), and one or more interfaces to external devices (e.g., computers, PDAs, and the like). The mobile device may also include a memory or data store.

A dental practice may not always have the best suited shade-base in a desired material in its inventory for upcoming patient restorations. As a result, most practices retain an extensive supply of CAD/CAM blocks to best select base shades for a patient's restoration. Furthermore, additional characterizing stains and glaze supplies are also retained in inventory to enhance the quality of the restoration for clients.

Advancements in mobile phone, mobile application, and location-based technologies have enabled broad platforms for matching users with needs to users with the ability to meet those needs. Such services include, but are not limited to, ride hailing services (like as Uber and Lyft) and food delivery services (like as DoorDash and UberEats). Such platforms would make it possible to extend the supply of restoration materials of a single practice to an entire network of dental practices in a given area.

CAD/CAM machines typically cost on the order of a few of hundred thousand dollars and represent a major investment for some practices. Depending on a patient population and their respective dental needs, such devices may go through feast or famine use cycles where there is an overdemand for the manufacturing services of the CAD/CAM system on one day but then underutilization on another day. Obviously, there is an economic interest for the dental practice to keep a steady state of use and billings associated with the device so that the machine will pay for itself. For example, even in a simple practice with 2 dentists and one CAD/CAM machine, one dentist may be blocked from using the machine until a restoration design completes the baking process in the oven, but a nearby dental practice may have a comparable idle machine that the other dentist could employ—a result that would help both practices.

Another factor in the economic success of such systems is the quality of restoration staining and glazing. A practice that can manufacture restorations quickly but does not match the aesthetic needs of its patients with skillful staining and glazing will not find optimal use of their CAD/CAM system. As many lab technicians can attest, there is an art to staining and glazing restorations. Incorporating some of this artful knowledge into CAD/CAM systems would continue to add to their value as an indispensable tool for the modern dental practice.

While advancements in CAD/CAM dentistry have allowed dentists to essentially have an "in-house" lab process with in the practice, it has yet to provide the dental practice with a predictable and biomimetic esthetic outcome for the dentist, similar to what a dental lab would produce. To date, after the dentist has chosen the preferred material and block, the dentist or the dental assistant still uses a physical shade-matching guide to select the chroma, value, hue for a myriad of dental material blocks~all of which have very different esthetic outcomes—and, from there, the dentist or dental assistant then characterizes the tooth based on his or her memory of what the tooth should look like. As dental medicine has become more specialized, this also includes dental laboratory training. In other words, the aforementioned techniques that laboratory technicians receive years of training are not as predictably transferrable to dentists or dental assistants. Embodiments of the present disclosure describe methods to predictably and reliably meld the technical and esthetic aspects of prosthetic tooth fabrication from both disciplines, the lab and dentist.

What is needed is a system that integrates CAD/CAM dentistry with machine learning, supply management, shade matching technologies and staining/glazing instructions coupled to delivery platforms to make it easy for dental practices to design the best restorations for patients, identify the best shade options given their budget and readily available supply of materials and capacity, and a platform to deliver those restorations quickly and efficiently.

Figure 1D:
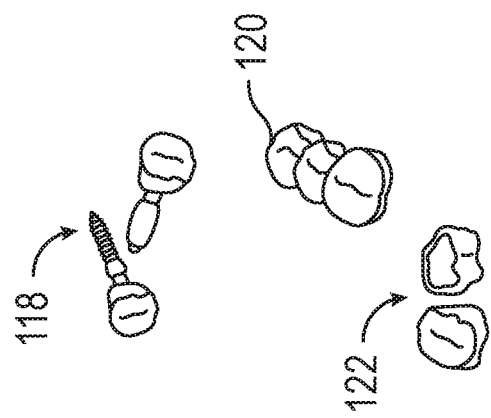
Figure 1C:
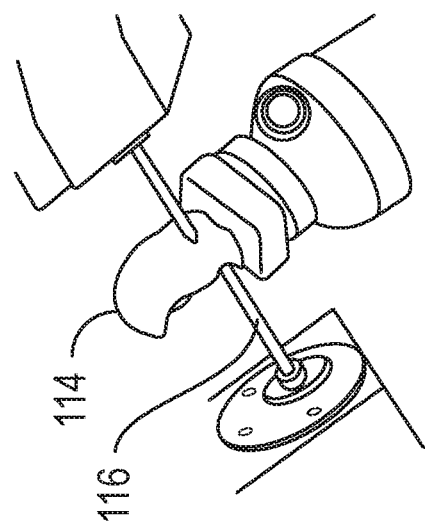

FIG. 1A illustrates a system and process for the manufacture of dental prosthetic items 100. The dental manufacturing system and method 100 may be a CAD/CAM system that includes a computing device 102, which is a computing system complete with keyboard, mouse, display and may be on a portable housing (for moving between the different operatories in a dental office). The system 100 includes a special camera device 104 for taking images of the patient's mouth for the purpose of designing the necessary restorative components. The system 100 includes an optional manufacturing component 106a which enables the dentist to manufacture the restorative component from raw materials and an oven 108 which enables the dentist to bake the milled restoration with optional stains/glazes for greater strength, color matching, and aesthetics. The manufacturing component 106a is shown in perspective schematic view 106b in FIG. 1K to illustrate the high level components therein, including but not limited to structural frames 106c, motors 106d, tools 106e, spindles 106f, and rails 106g. Generically speaking, the frames 106c move horizontally on the rails 106g while housing the motors 106d that drive the spindles 106f to give the tools 106e the degrees of freedom necessary to mill the restorations. Though not shown in schematic 106b, some CAD/CAM systems 100 have a third motor in the center to hold and spin the restoration while it being milled simultaneously by tools 106e on the spindles 106f.

Figure 1B:
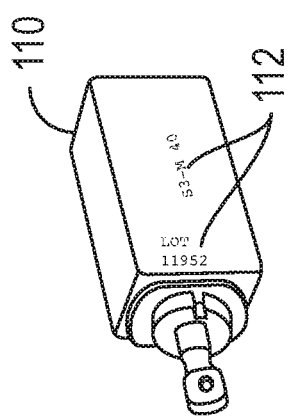

FIG. 1B illustrates exemplary blocks associated with the dental manufacturing system and method 100. Block 110 is an unprocessed block complete with markings 112 describing the attributes of the block (such as lot number, inventory number, etc.). Block 114 is one that is actively being machined by the burrs 116 in dental system 100. Blocks 118, 120, and 122 represent blocks that have completed the manufacturing process in dental manufacturing system 100. Specifically, block 118 is an implant block, block 120 represents a bridge block, and block 122 represents a crown block.

Figure 1E:
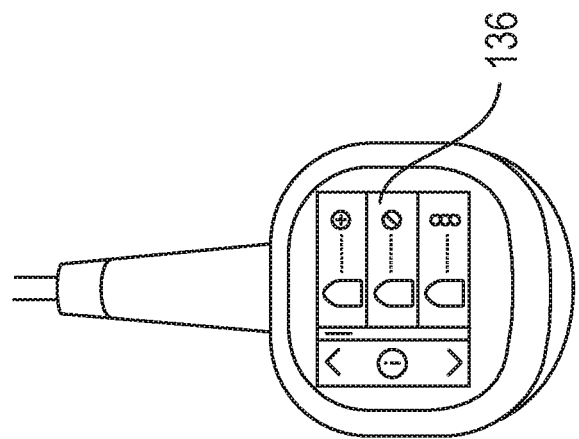
Figure 1E:
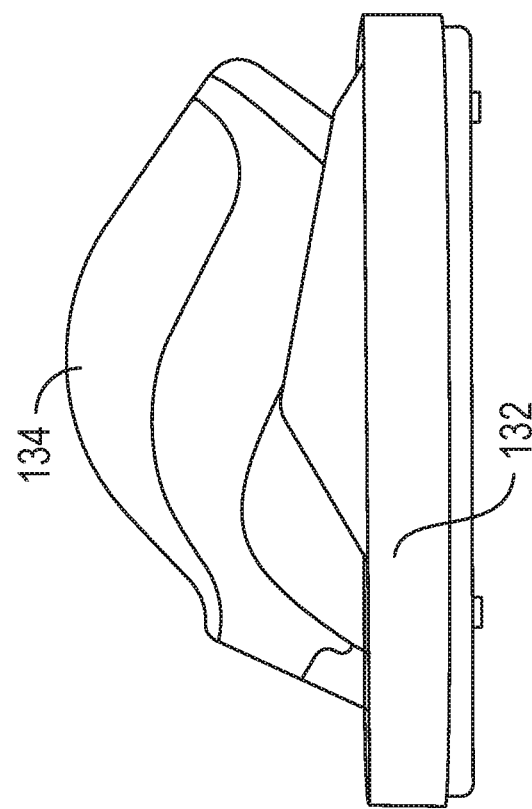
Figure 1K:
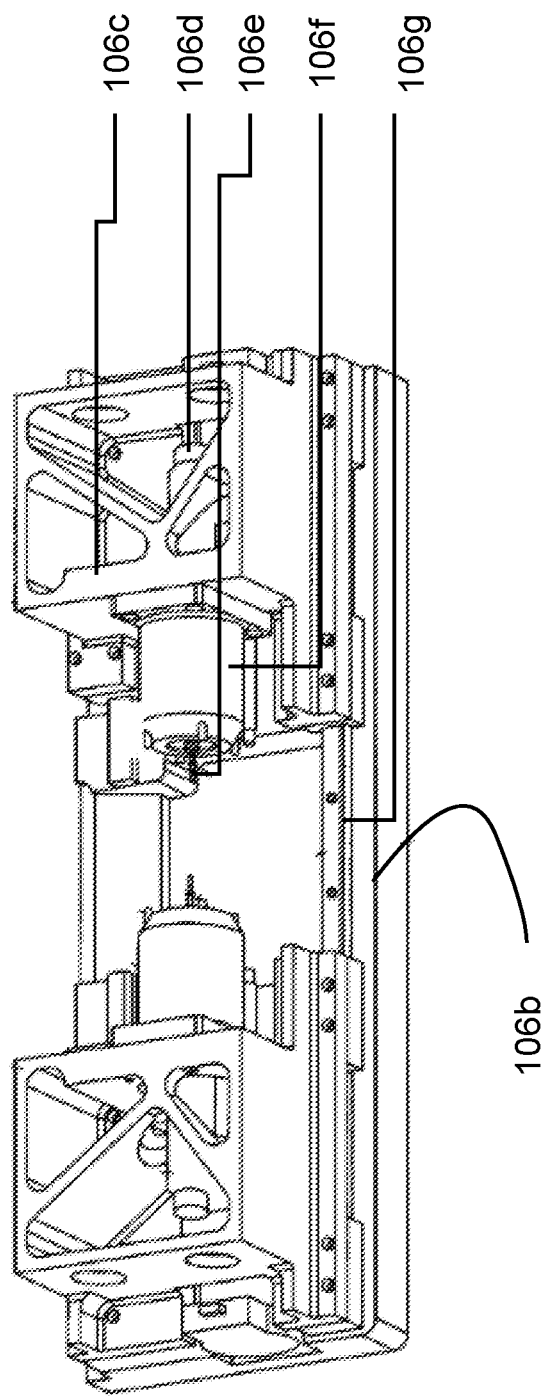

FIG. 1E illustrates an exemplary spectrophotometer system 130. The spectrophotometer system includes a charging station 132, a spectrophotometer 134, and an output display 136. The spectrophotometer 134 allows the dentist to measure the intensity of light in part of the spectrum as it is emitted by the patient's tooth (or adjacent teeth) involved in the restorative procedure. The results of the spectrophotometer on the output display 136 provide shade information for the tooth (for matching the manufacturing block for the restorative procedure) and/or the bleach index number (for tooth whitening).

FIGS. 1F-1J illustrate reduction coping via the sequence of images. In FIG. 1F, a crown 146 is designed to go over a tooth 142 in need of restoration. However, given the strength of the material used to make the crown, the minimum depth for the material 144 is not met. This means that the crown runs the risk of breaking if put into service. In FIG. 1G, reduction coping is a sheath of material 148 (usually acrylic/resin or cast metal) that fits over the tooth 142 that shows the dentist the area 150 of the tooth 142 that needs to be ground down in order to meet the minimum depth requirement. In FIG. 1H, once the tooth 142 is adjusted accordingly, the crown 146 can be made with the minimum depth requirement met 152. Reduction coping works for adjusting the top of the tooth 154 in FIG. 1I as well as the side of the tooth 156 in FIG. 1J. While the current design system indicates to the dentist when he or she has not achieved minimal thickness or reduction, the manufacturing/fabricating feature of the crown design can, and, is often over-looked and over-ridden, such that the crown is fabricated anyway. Particularly, in a teaching environment such as a school, should the over-riding occur, by default, the milling unit will automatically indicate to the user that a reduction coping will be fabricated before the crown. The type of resin or acrylic block that can be used for the reduction coping would have to be inserted and milled before the crown could be. From there, the dentist or dental student can utilize the reduction coping, as he or she would if the lab determined inadequate reduction and sent one back with the finished crown case. This "REMEDIATION MODE/FEATURE/EMBODIMENT" can be turned on or off per user preference.

Figure 2A:
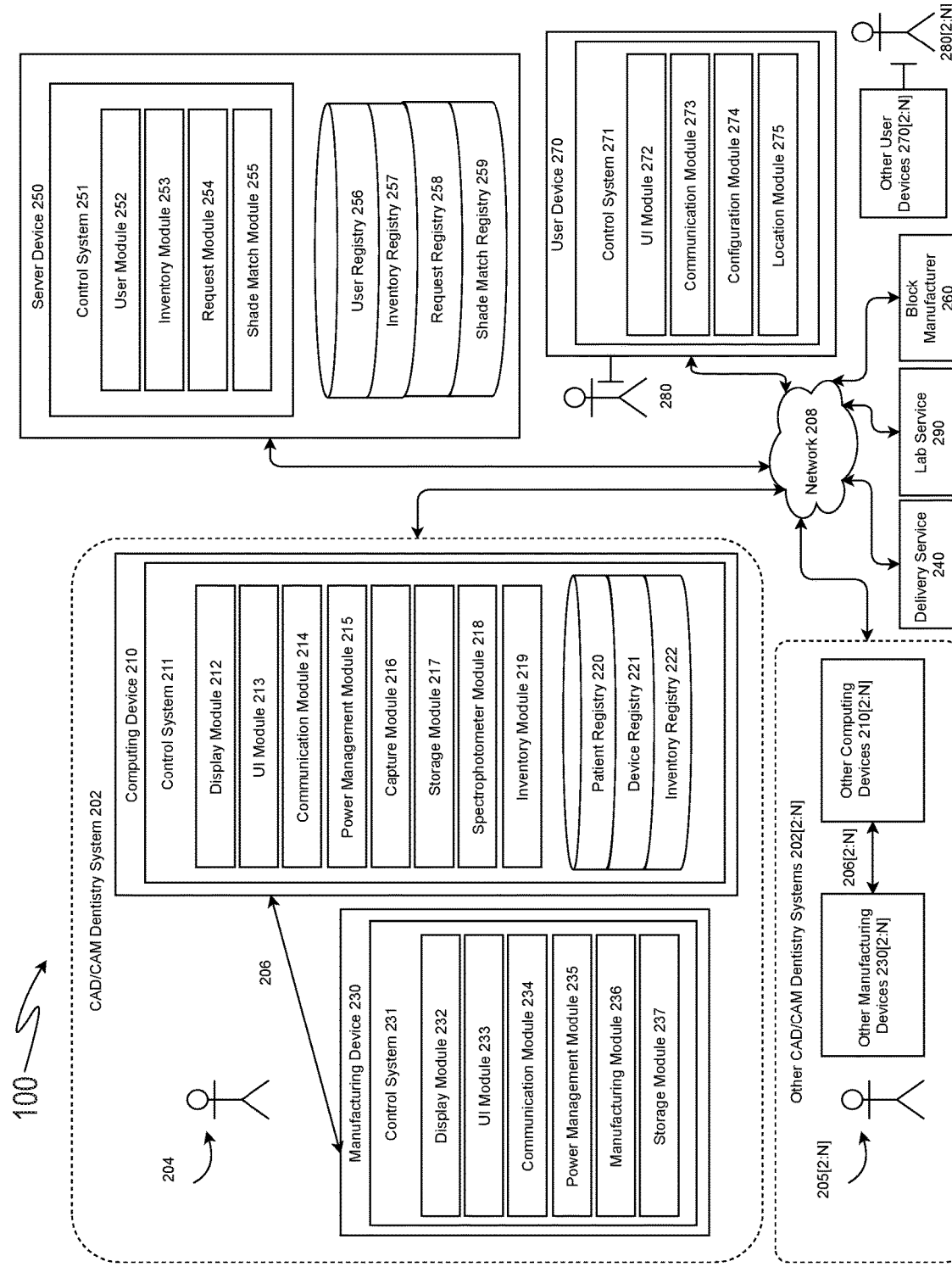
FIG. 2A illustrates an embodiment of the present disclosure for the system of shade matching and localized laboratory aesthetics for restorative design in dentistry.

FIG. 2A illustrates an embodiment of the present disclosure for the dental manufacturing system and method 100 with shade matching and inventory management. The system 100 includes one or more CAD/CAM dentistry systems 202[1:N] (where N represents any number of systems) associated with one or more system operators 204[1:N], server device 250, one or more user devices 270[1:N] (where N represents any number of devices, and the N for systems may be different from the N for devices) associated with one or more device operators 280[1:N], a delivery service 240, a lab service 290, and block manufacturer 260, all connected by a network 208. For clarity, when dental operators with CAD/CAM systems are acting as a supplier to a requesting dentist 204, they shall be indicated as operator 205[2:N]. It is recognized that a requesting dentist 204 in one transaction could be a supplying dentist 205 in another transaction. The network 208 may be wired (Ethernet), wireless (Wi-Fi, WiMAX, other IEEE wireless standards), cellular (4G, 5G, etc.), private, or public. Server device 250, block manufacturer 260, delivery service 240 and lab service 209 may be implemented as one single server or a group of servers. In some embodiments, server device 250 could be implemented in distributed fashion across the CAD/CAM Dentistry systems 202[1:N], leveraging software utilities (like Hadoop) for using a network of many computers to solve complex problems (like artificial intelligence such as machine learning problems discussed herein) and leveraging 5G for sending greater amounts of data at between the network of computers.

The one or more CAD/CAM dentistry systems 202[1:N] associated with one or more system operators 204[1:N] comprise a computing device 210[1:N] and a manufacturing device 230[1:N], hereinafter referred to as 210 and 230 respectively for ease of reading the specification. The one or more CAD/CAM dentistry systems 202[1:N] may also have an oven (such as the Denstply Sirona SpeedFire oven 108, or a conventional oven, or the like).

The computing device 210 is used by the system operators 204[1:N] (usually a dentist or licensed professional or delegate like an assistant—hereinafter referred to as 204 for ease of reading this disclosure) to scan the patients mouth and design the restorative dental service needed (inlay, onlay, crown, etc.). The computing device 210 comprises a control system 211, a display module 212, a user interface module 213, a communication module 214, a power management module 215, a capture module 216, a storage module 217, a spectrophotometer module 218, and inventory module 219, and a patient registry 220, a device registry 221, and an inventory registry 222.

The control system 211 controls the different modules of the computing device 210. The display module 212 includes one or more displays for relaying information to the system operators 204, such as a touch screen, computer screen or the like. The user interface module 213 takes inputs from the system operator 204 and may include as a mouse, keyboard, touchscreen, wand, camera, and the like, and the associated hardware and software to receive such inputs. The communication module 214 communicates 206 information between the computing device 210 and the manufacturing device 230 and/or other elements of the system 100 accessible through the network 208. The power management module 215 puts the device into sleep or power save mode and in some embodiments may charge user input elements 213 (like the wand or spectrophotometer). The capture module 216 takes photos of the patients mouth for purposes of designing the restoration and may be included in the wand as a part of the user interface module 213. The storage module 217 stores programs and data in the normal course of operating the computing device 210.

The spectrophotometer module 218 is capable of receiving input from spectrophotometer 134 and is used to determine shade information for the patient's teeth and stores information in the patient registry 220. In some embodiments, the spectrophotometer module 218 is also used to determine shade information for unmanufactured blocks 110 to be milled by the manufacturing device 230 and/or manufactured blocks (118, 120, 122 shown in FIG. 1D) that may have stains or glazes added to the base material of the block as part of the finishing process. In some embodiments, the spectrophotometer module 218 is built into the capture module 216 of the computing device 210. In other embodiments, the spectrophotometer module 218 (e.g., spectrophotometer 134) is a peripheral for the computing device 210 with the ability to transmit data to the computing device 210 over a communications interface (wireless, Ethernet, USB, Thunderbolt, etc.) through the communications module 214.

The inventory module 219 collects information about the inventory of blocks that the operator 204 has available onsite for restorative procedures and interacts with the inventory registry 222. In some embodiments, the inventory module 219 includes a bar code reader that is able to quickly scan a bar code associated with an order of dental supplies so that it is possible to retrieve the details of the order and update the inventory registry 222 accordingly. In other embodiments, the inventory module includes a reader that can process the attributes 112 written on the individual blocks to update the inventory registry 222. In some embodiments, this inventory module 219 is built into the capture module 216 of the computing device 210. In other embodiments, the inventory module 219 interacts with the block manufacturer 260 or reseller to update the inventory registry 222 based on order information. The device registry 221 retains information about devices capable of connecting to system 202.

The manufacturing device 230 comprises a control system 231, a display module 232, a user interface module 233, a communication module 234, a power management module 235, a manufacturing module 236, and a storage module 237. The manufacturing device 230 is connected to the computing device 210 via a communications link 206, which may be wired (Ethernet), wireless (Wi-Fi, WiMAX, other IEEE wireless standards), or other device communications protocols (Bluetooth, USB, Serial, cellular LTE or 5G, etc.). In some embodiments, the communication link 206 may use the same network used to communicate with other devices over the network 208. In other embodiments, it may be a separate secure communication link between the computing device 210 and the manufacturing device 230.

The control system 231 controls the different modules of the manufacturing device 230. The display module 232 includes one or more displays for relaying information to the system operators 204, such as a touch screen, computer screen or the like. The user interface module 233 takes inputs from the system operators 204 and may include as a mouse, keyboard, touchscreen, buttons, keypad, soft keys, camera, and the like, and the associated hardware and software to receive such inputs. The communication module 234 communicates information between the manufacturing device 230 and the computing device 210 via the communications link 206 and/or other elements of the system 100 accessible through the network 208. The power management module 235 puts the device into sleep or power save mode and may also charge any portable peripherals associated with the manufacturing device 230. The manufacturing module 236 makes the restorative dental elements (inlay, onlay, crowns, etc.) from raw blocks 110 according to design files created by the system operator 204 on the computing device 210 and received by the manufacturing device 230 over the communications link 206. The storage module 237 stores programs and data in the normal course of operating the manufacturing device 230.

FIG. 2A further illustrates a server device 250 connected through a network 208 to the CAD/CAM dentistry systems 202. The server device 250 comprises a control system 251, a user module 252 that interacts with the user registry 256, an inventory module 253 that interacts with the inventory registry 257, a request module 254 that interacts with the request registry 258, and a shade match module 255 that interacts with the shade match registry 259. The registries (256, 257, 258, 259) may be implemented in different databases or graphs, an aggregate database or graph, or combinations therein.

The user module 252 of server device 250 is employed for user interactions with the system 100—logins, setting/changing profile/attributes, etc. The inventory module 253 is used in collecting and reporting inventory of the users of the system 100. The request module 254 is used to collect, track, and report requests for inventory blocks 110 and/or milled restoration blocks (118, 120, 122) that involve the delivery service 240. The shade match module 255 is used for recording anonymized shade information of patients and the actions taken with respect to recommendations from the system 100.

In some embodiments, the system 100 may be connected through the network 208 with a block delivery service 240. Block delivery service 240 may be a ride sharing service (like Uber or Lyft) that can be used to pick up blocks from other dental practices that have the block in inventory or other dental supply companies that have the block in inventory. In some embodiments, the blocks will also be already milled so that a final product is picked up by the staff of the delivery service. In other embodiments, the delivery service is a traditional shipping company (UPS, FedEx, DHL, etc.). In other embodiments, the delivery service is a courier service, like the ones that operate in large cities to provide intra-day delivery. In still further embodiments, the delivery service is offered by a dental supply company (like Patterson) or a manufacturer (like Dentsply Sirona).

FIG. 2A further shows a lab service 290 connected to network 208. The lab service 290 is a full dental laboratory solution that provides, among other services, reduction coping services that generate acrylic/resin and/or cast metal copings. In some embodiments, the lab could be used to provide characterization services (staining/glazing) on restorations designed and manufactured by the CAD/CAM system. However, in general, sending out restorations like this would add time and would be reserved only for the most discerning patients.

FIG. 2A shows a block manufacturer 260 connected to network 208 that is the manufacturer of the blocks 110 used for dental restorations. In some embodiments, this is the primary manufacturer (like Dentsply Sirona for CEREC blocks, etc.). In other embodiments, it is a reseller of the blocks used for dental restorations. Block manufacturer 260 is the original supplier of restoration blocks 110 for the dentist 204 to build up the local inventory that is used for exchanging with other dentists 205[2:N] in the specified geographic area according to embodiments of the present disclosure.

FIG. 2A shows a User Device 270 (e.g., mobile phone) is connected through network 208 and may be used to interface with the delivery service 240 to schedule pickups for inventories. User Device 270 comprises a control system 271, a user interface module 272, a communications module 273, a configuration module 274, and a location module 275. User Device 270 may be a mobile device, such as a smart phone or a tablet. Control system 271 controls the operation of the device 270. User interface module 272 takes inputs from the device operator 280 and may include a keyboard, touchscreen, camera, bar code reader, scanner, and the like, and the associated hardware and software to receive such inputs. The communication module 273 communicates via the network 208 to the other devices of the system (202, 250, 240, 260, 270, 290) via wired and/or wireless, public and/or private networks, using the Internet and/or cellular networks. Configuration module 274 is used to configure settings on the User Device 270, including which applications to install and configure on the device. Location module 275 is used to identify the current location of the user device 270 via GPS, cell tower triangulation, Wi-Fi and the like. Applications (apps) installed on mobile device 270 are used to interface with the delivery service 240 to schedule pickups for inventories according to embodiments of the present disclosure. These apps may be developed and provided by the delivery service 240 or may be developed and provided by the block manufacturer 260 or by an independent vendor (such as a dental supply company like Patterson or other implementer of system 100) or some combination thereof.

Figure 2D:
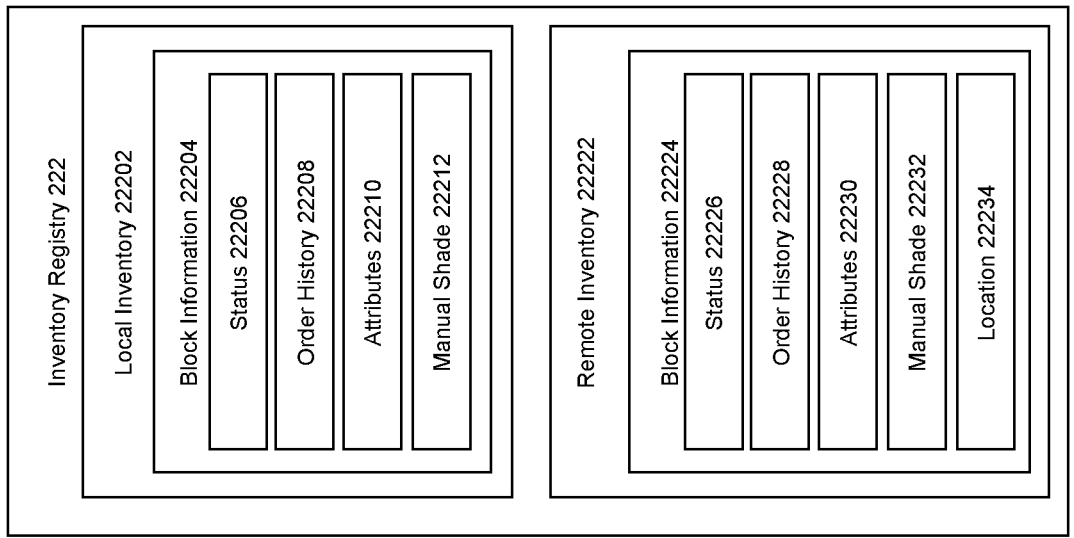
FIG. 2D illustrates details about the inventory registry of the system of shade matching and localized laboratory aesthetics for restorative design in dentistry from FIG. 2A.
Figure 2C:
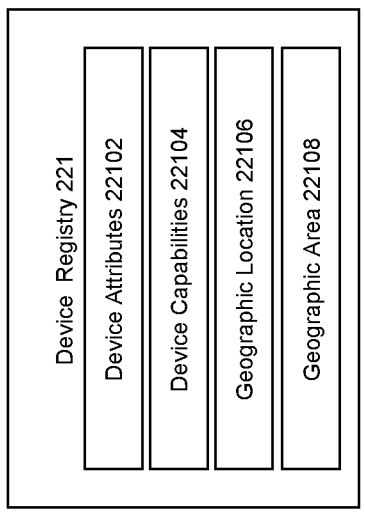
FIG. 2C illustrates details about the device registry of the system of shade matching and chairside laboratory aesthetics for CAD/CAM restorative design tin CAD/CAM dentistry from FIG. 2A.
Figure 2B:
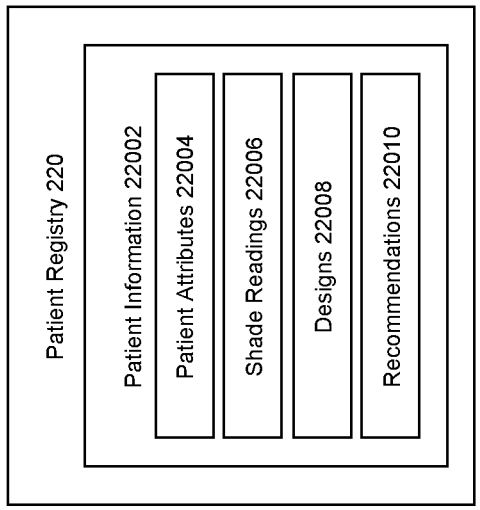
FIG. 2B illustrates details about the patient registry of the system of shade matching and localized laboratory aesthetics for restorative design in dentistry from FIG. 2A.

FIG. 2B illustrates details about the patient registry 220 used to store patient shade information for the system 202 of shade matching and restoration design in CAD/CAM dentistry from FIG. 2A. Patient registry 220 comprises patient information 22002 which comprises patient attributes 22004, shade readings 22006, designs 22008, and recommendations 22010. Patient information 22002 may reside in the computing device 230 or may be inherited or accessed from other electronic medical health record systems used by the dentist 204 that may be able to interact with the computing device 230. Patient attributes 22004 include standard patient demographic information unique to a particular patient, including but not limited to name, address, date of birth, employer, guardians (for minors), insurance carriers, history of service, etc. Shade readings 22006 include one or more spectrophotometric readings associated with the one or more restoration procedures for the patient identified by the patient attributes 22004. Designs 22008 reflect the different restoration designs (crowns, onlays, implants, etc.) that the dentist has assembled for the restoration procedures for the patient identified by the patient attributes 22004. In some embodiments, anonymized source images of the patient used by the dentists 204 in the development of a particular restoration design may also be captured and stored in user designs 22008. In still further embodiments, information about the final restoration put in place on the patient (its shade readings, materials, staining/glazing patterns) may also be captured and become part of the designs 22008. Recommendations 22010 include the block recommendations for a particular design 22008 and particular shade reading 22006 for a particular restoration procedure for the patient identified by the patient attributes 22004. In some embodiments, the patient information 22002 includes only those patients served by the particular location associated with computing device 210. In other embodiments, patient information 22002 includes all patients associated with the practice.

Figure 4A:
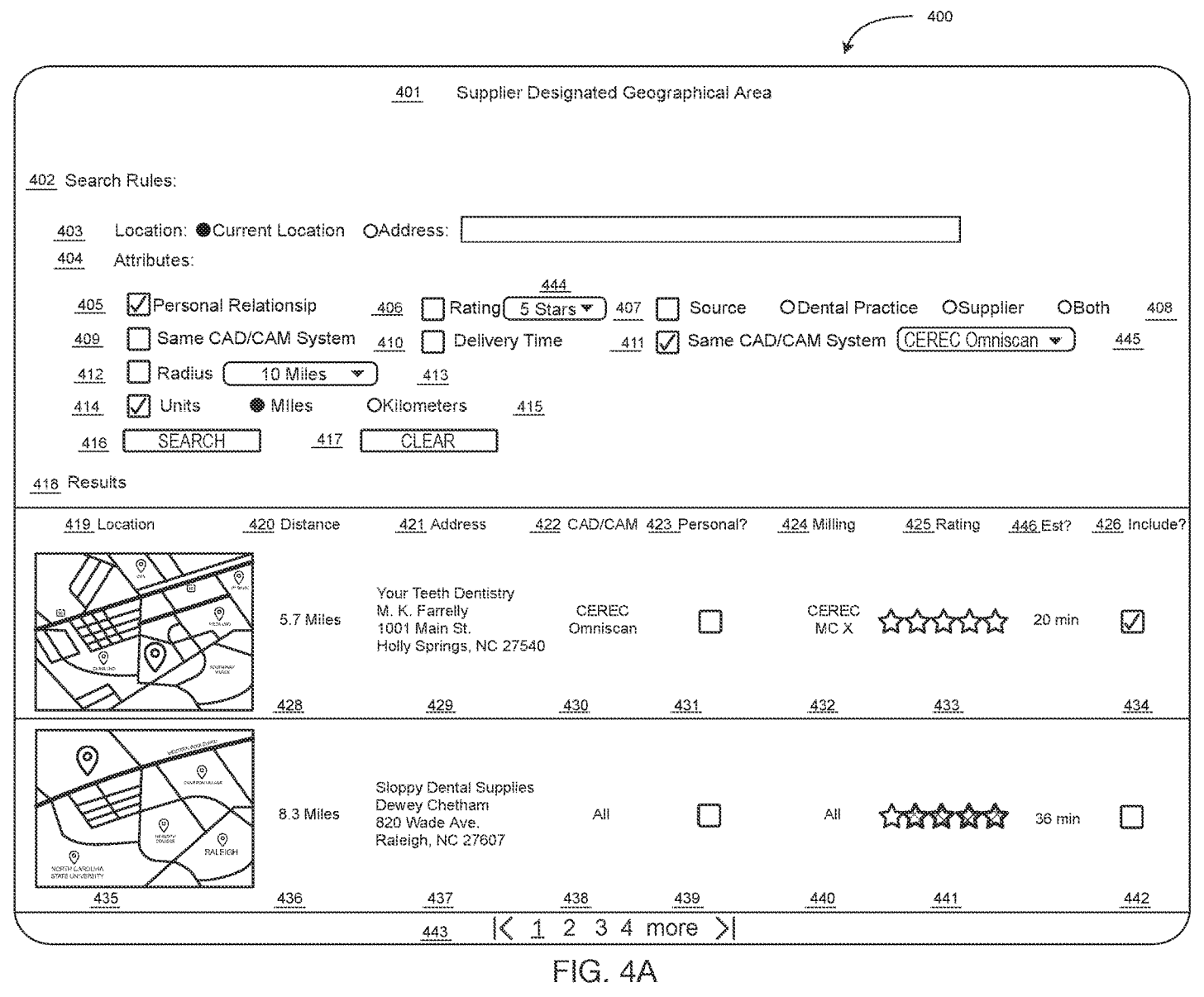
Figure 4B:
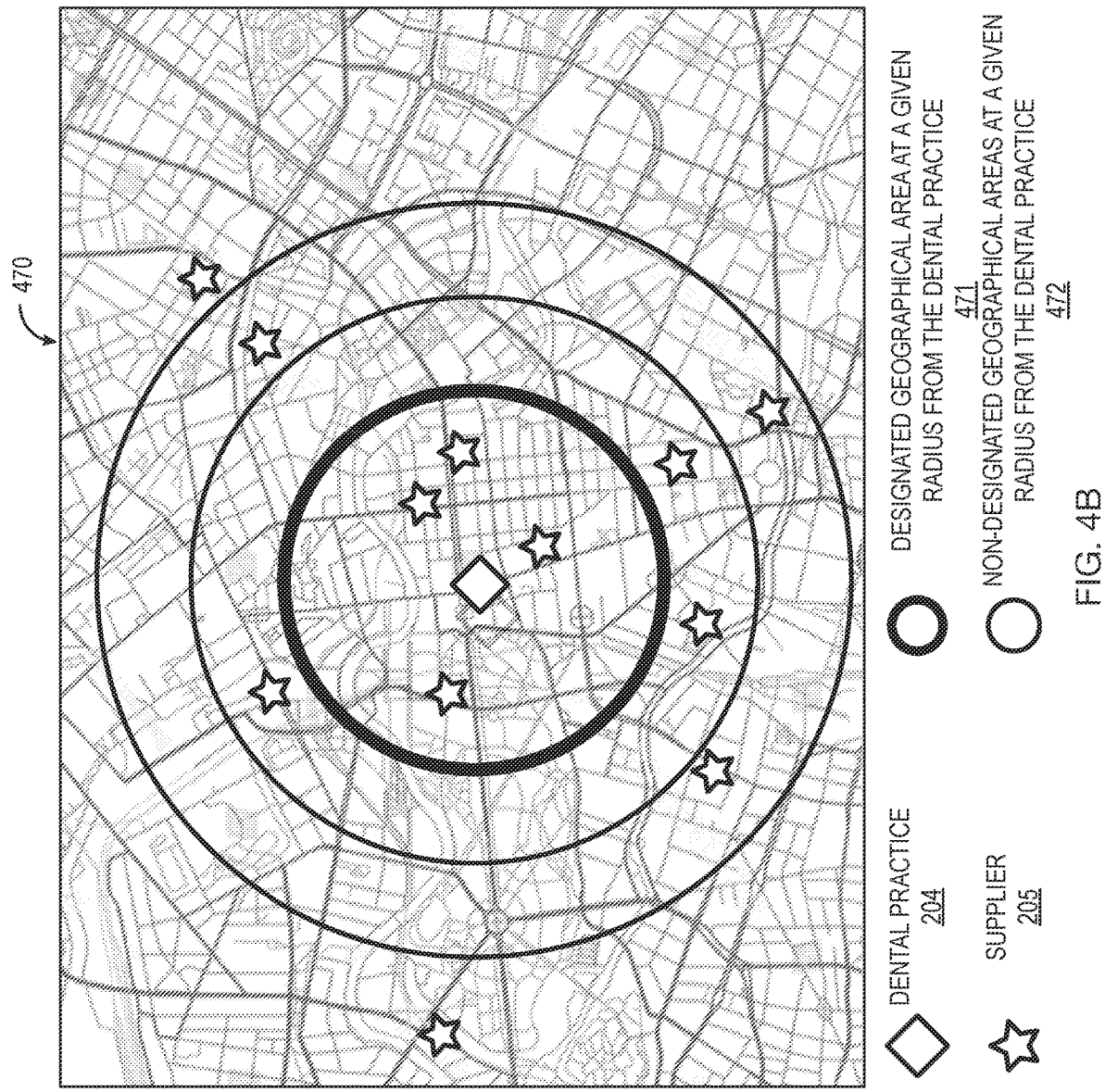
FIG. 4B illustrates an example of the definition of a designated geographical area from which dental supplies may be sourced according to one embodiment of the present disclosure.

FIG. 2C illustrates details about the device registry 221 of the system 202 of shade matching restoration design in CAD/CAM dentistry from FIG. 2A. Device registry 221 comprises device attributes 22102, device capabilities 22104, geographic location 22106, and geographic area 22108. Device attributes 22102 comprise information such as the manufacturer, model number, serial number and the like. In some embodiments, device attributes may include a status, like the device is on, it is available to make a restoration, it is in maintenance mode, can it accept remote control sessions, etc. Device capabilities 22104 include information such as which types of manufacturing devices 230 the computing device 210 can work with as well as which types of blocks 110 it can accept for milling. In some embodiments, similar attributes of the manufacturing device 230 and/or the oven 108 are also captured. Geographic location 22106 represents the location of the computing device 210. This can be an address, latitude & longitude coordinates, what3words, or the like. In some embodiments, a GPS receiver can be used to automatically determine the location of the computing device 210. In some embodiments, the GPS receiver may be internal to the computing device 210 or can be attached to the computing device 210 as a peripheral. Or in some embodiments, the location of the computing device 210 can be inherited by the location reported by mobile devices 270 in proximity to the computing device 210. In still other embodiments, the manufacturing device 230 may have its own GPS receiver, peripheral, or proxy to determine its location. In further embodiments, the location of the computing device 210 may be retrieved from the manufacturer 260 who keeps a record of CAD/CAM customer installations (such as cerecdoctors.com). Geographic area 22108 comprises information about the geographic area from which to draw inventory. This can be a zip code area, a radius (such as a 5 mile radius from the location of the computer device 210, as shown in FIG. 4B), arbitrary polygons around the location of the device 210, or simply a list of known providers in proximity to the device 210. Because each dental practice may have several operating offices, some with manufacturing capabilities 230 and some without, each computer device 210 can have its own geographic area.

FIG. 2D illustrates details about the inventory registry 222 of the system 202 of shade matching and restoration design in CAD/CAM dentistry 202 from FIG. 2A. Inventory registry 222 comprises local inventory 22202 and remote inventory 22222. Local inventory 22202 refers to what inventory of blocks is available at the same location as the CAD/CAM system 202. Local inventory 22202 includes block information 22204 that comprises status 22206, order history 22208, attributes 22210, and manual shade 22212. Status 22206 refers to the availability of the block—whether it is available in inventory, earmarked for a restoration on site, earmarked to fulfil a request at a remote location, the milling status (is it milled yet), and the like. Order history 22208 includes information on when the block was ordered, including the order date, vendor who supplied the block, other blocks ordered at the same time, etc. Attributes 22210 of the block include information about the block, like material type, lot numbers, dimensions, shade, etc. Manual shade 22212 includes manual information about the shade of the block that is generated by using a spectrophotometer module 218. Manual shade measurements may allow a dental practice to more closely align restorations with their patients' teeth by using the same spectrophotometer to measure the tooth shade and the shade of the restoration. It also allows the dentist 204 to capture shades of particular stains and glazes that they may use with that block for patients.

Figure 2G:
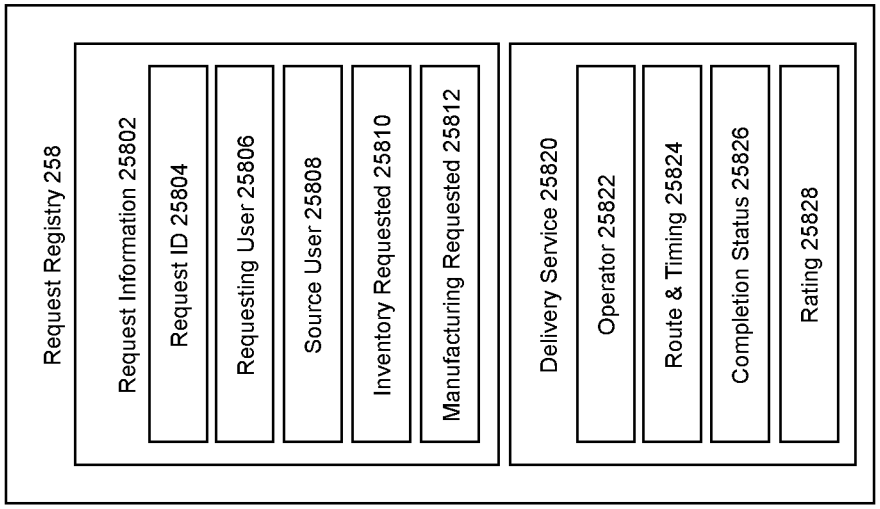
FIG. 2G illustrates details about the request registry of the system of shade matching and localized laboratory aesthetics for restorative design in dentistry from FIG. 2A.

Remote inventory 22222 in FIG. 2D includes block information 22224 that comprises status 22226, order history 22228, attributes 22230, manual shade 22232, and location 22234. The remote inventory 22222 comprises information similar to the local inventory reported by other practices within the designated geographic area 22108 to a particular practice. In some embodiments, it may also include inventory available from the block manufacturer 260 or a reseller that may be in the designated geographical area 22108. Status 22226 refers to the availability of the block— whether it is available in inventory, earmarked for a restoration on site, earmarked to fulfil a request at a remote location, the milling status (is it milled yet), and the like. Order history 22228 includes information on when the block was ordered, including the order date, vendor who supplied the block, other blocks ordered at the same time, etc. Attributes 22230 of the block include information about the block, like material type, lot numbers, dimensions, shade, quantity, etc. Manual shade 22232 includes manual information about the shade of the block that is generated by using a spectrophotometer module 218 (if available). Location 22234 includes information about the location of the block, i.e. the dental practice and/or supplier that has the block in inventory. In some embodiments, the remote inventory 22222 is a cache of information that is available from the inventory registry 257 on the server device 250 (of FIG. 2A), either in part or in whole, and synced either periodically or in response to user activity or order history. In still further embodiments, the remote inventory 22222 caches only the favorite or most common suppliers 205[2:N] used by a dentist 204. In this respect, the dentist 204 always has accurate inventories of the most frequent suppliers. FIG. 2E illustrates details about the user registry 256 of the system 100 of FIG. 2A. User registry 256 comprises user accounts 25602 and user attributes 25604 that comprise user preferences 25606, user address 25608, user systems 25610, user designs 25612, user ratings 25614, user social graph 25616, and user usage history 25618. User accounts 25602 allow the user (dentists 204, suppliers 205[2:N], manufacturer 260 or reseller, delivery operators 280, etc.) to log into the system. In some embodiments, user accounts can leverage federated identity protocols (e.g., security assertion markup language (SAML), OAUTH authorization protocol, etc.) to permit token based access to the system based on authentication credentials from other sites. User preferences 25606 comprise preferences regarding the use of the system, such as software configuration settings and preferred/favorite suppliers, delivery companies, and the like. User address 25608 includes the primary operating location of the dentist user 204. User systems 25610 include information about the CAD/CAM dentistry systems 202 associated with the dentist user 204. In some embodiments, the locations of all CAD/CAM dentistry systems 202 associate with the dentist user 204 are captured in user address 25608. User designs 25612 include the anonymized restoration design files from the dentist 204 for different patients for which the system is employed to find available blocks and milling services. In some embodiments, the user designs 25612 may be coupled with an artificial intelligence such as machine learning process to potentially provide other dentist users 205[2:N] of the service with design ideas for similar restoration situations with their patients. Artificial intelligence shall be defined for the purposes of this disclosure shall mean computer systems performing tasks that normally requiring human intelligence such as decision making, planning, and the like. An example would be machine learning which is a machine which improves automatically through repetition and experience. In still other embodiments, anonymized source images of the patient used by the dentist users 204 in the development of a particular restoration design may also be captured and stored in user designs 25612 to further enhance the machine learning process applied to the system to serve as a source for restorative practices.

For example, an anonymized picture of the patient's tooth is captured along with the shade measurement so that the dentist user (or assistant) 204 who is ultimately providing the characterization (i.e. stains and/or glazes) for the restoration will have a reference image. Notes about how the characterization will be done can also be captured, including the assistant 204 who will be completing the characterizations. This would enable better shade matching and characterization for patients with teeth that are not uniform in color and/or have special considerations, and it would enable a dentist user 204 to select the work of a particular assistant at a particular practice if the dentist user 204 felt like that particular assistant generated good work that they wanted to use for patients. Other embodiments would link the inventory management to the staff schedule so that the dentist 204 could get the right inventory blocks and the right assistant to produce the restoration that is desired.

In another example, the anonymized source images of the patient used by the dentists 204 in the development of a particular restoration design would include several pieces of information, including but not limited to: tooth number affected by the restoration, spacing of adjacent teeth, quality of the gums, jawline angles in the plane of the teeth, tooth shape including any taper or anomalies, tooth angle with the jawline (orthogonal to the plane of the teeth), quality of the jawbone and adjacent teeth, anonymized patient data (age range, overall health, previous mouth work or trauma, etc.), geometry of opposite teeth for bite impact, etc.) This data could be fed into a machine learning process along with the doctor's restoration design for that patient. In this respect, when data 25612 from thousands or more patients are collected, the system 100 could receive a particular patient scan, run a machine learning process with the scan against the scans of other patients and their associated restorative designs and suggest an initial design restoration for the particular patient scan, as outlined in FIG. 3C and FIG. 6D. In some embodiments, the machine learning processes would include translation processes for normalizing the geometry of the stereo lithic file and genetic processes for generating the suggestions.

It is important to note that the normal process for creating a restoration includes the milling of the restoration from a block, followed by an optional step where stains and glazes are added to further enhance the matching of the restoration for the patient, and then baking the restoration in the oven before producing the final product. Embodiments of the present disclosure will allow a dentist the option of either ordering raw blocks from another supplier, ordering the milling of a raw restoration (i.e. one that is milled just from the block), ordering a fully characterized and milled block (i.e. one that has not been baked yet in the oven), and/or ordering a completed end restoration, complete with milling, characterization, and baking.

User ratings 25614 include ratings given by users of the system to various suppliers 205[2:N] as shown by 425 in FIG. 4. User social graph 25616 permits the application of a social graph to the system, based on users who regularly employ the system for regular transactions. For example, if a particular dentist 204 always exchanges CAD/CAM blocks with particular other dentists or suppliers 204[N:2], then this would be captured in the user social graph 25616. In some embodiments, the social graph 25616 comprises a professional social network (such as LinkedIn®, Facebook®, dental association, etc.). User usage history 25618 keeps track of the transactional details between users of the system 100. This usage information may inform the social graph 25616.

In some embodiments, patient data collected by the system (such as the restoration designs for the patient 25612 and the patient information 22002) could easily be re-associated with another dentist 204, should the patient relocate anywhere in the world. In some embodiments, server 250 in system 100 has an easy mechanism whereby the old dentist 204 can receive a request for their records in the system 100 to be reassigned to the new dentist 204. Proof of patient agreement with the transfer could optionally be part of the mechanism, and could leverage well known federated identity management techniques.

Figure 2F:
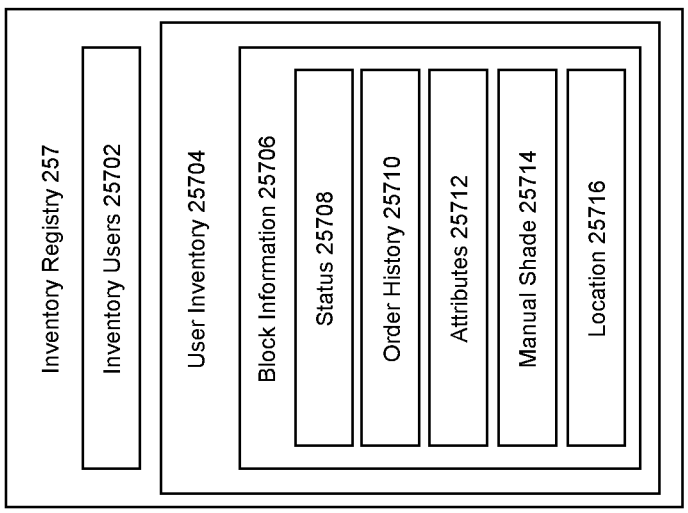
FIG. 2F illustrates details about the inventory registry of the system of shade matching and localized laboratory aesthetics for restorative design in dentistry from FIG. 2A.
Figure 2E:
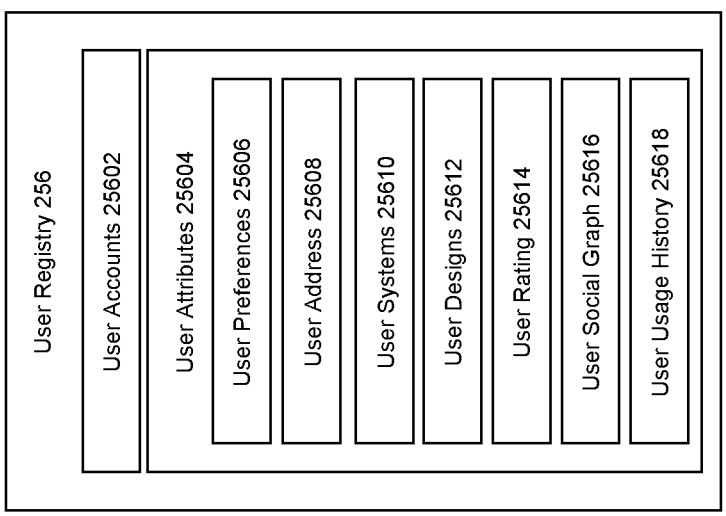
FIG. 2E illustrates details about the user registry of the system of shade matching and localized laboratory aesthetics for restorative design in dentistry from FIG. 2AA.

FIG. 2F illustrates details about the inventory registry 257 of the system 100 from FIG. 2A. Inventory registry 257 comprises inventory users 25702 (which include the users in the user registry 256) and their corresponding inventories 25704. User Inventory 25704 includes block information 25706 that comprises status 25708, order history 25710, attributes 25712, manual shade 25714, and location 25716. Status 25708 refers to the availability of the block—whether it is available in inventory, earmarked for a restoration on site, earmarked to fulfil a request at a remote location, the milling status (is it milled yet), and the like. Order history 25710 includes information on when the block was ordered, including the order date, vendor who supplied the block, other blocks ordered at the same time, etc. Attributes 25712 of the block include information about the block, like material type, lot numbers, dimensions, shade, quantity, etc. Manual shade 25714 includes a manual measurement of the shade of the block taken by the inventory user 25702. Location 25716 includes information about the location of the block, which is useful if users 25702 have multiple locations.

FIG. 2G illustrates details about the request registry 258 of the system 100 from FIG. 2A. Request registry 258 comprises request information 25802 and delivery service information 25820. Request information 25802 includes a unique request ID 25804, information about the requesting user 25806, the source user 25808, the inventory requested 25810, and the manufacturing requested 25812 (also called milling). In some embodiments, the manufacturing requested 25812 would include information as to whether characterizations (staining/glazing) should be applied to the product before delivery and which technicians should do the characterizations. Information about the requesting user 25806 may include all or some of the user attribute information 25806 associated with user accounts 25604 of the users of the system 204. Similar for source user information 25808. Inventory requested 25810 would include information about the blocks, shade, delivery deadlines, payment information, etc. that are associated with the request. Manufacturing requested 25812 information would include the stereo lithic (.STL) design files associated with the request. In some embodiments, the design information would be captured in a different file type (such as a .RST restructured text file or the like) and would be converted into a format for portability. In still further embodiments, the scan of the prepared tooth may similarly be converted or delivered in different necessary file formats, for example, if conversion between systems was required.

Delivery Service 25820 information comprises information about the operator 25822 who will be completing the delivery, the route and timing taken for the delivery 25824, completion status 25826, and the rating 25828 of the delivery operator 25822 and the delivery service 240.

Figure 2H:
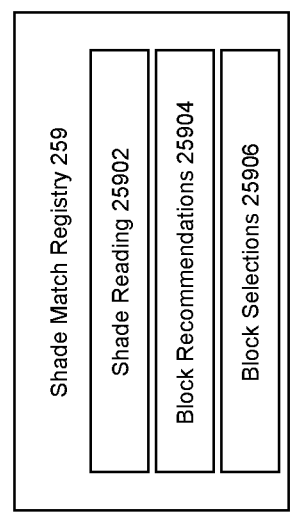
FIG. 2H illustrates details about the shade match registry of the system of shade matching and localized laboratory aesthetics for restorative design in dentistry from FIG. 2A.

FIG. 2H illustrates details about the shade match registry 259 of the system 100 of FIG. 2A. Shade match registry 259 comprises shade readings 25902, block recommendations 25904, and block selections 25906. Shade reading 25902 comprises shade readings for patients. Block recommendations 25904 contain the block recommendations made for the patient. In some embodiments, this is a running history of block recommendations. A patient may not initially get a restoration on the original date when one is discussed or identified. A dentist 204 may initially get some recommendations. But when the patient then decides to move forward with the procedure, the dentist 204 may need to update those recommendations. This running history is captured by block recommendations 25904 in some embodiments. Block selections 25906 then captures what blocks of the recommendations (or an entirely different block) that might be selected for a patient. The collective information of the shade match registry 259 can be used with machine learning to further hone recommendations and provide valuable insight to the block manufacturer 260. In some embodiments, information about characterizations done to the block selected are also captured to further enrich machine learning.

Figure 3A:
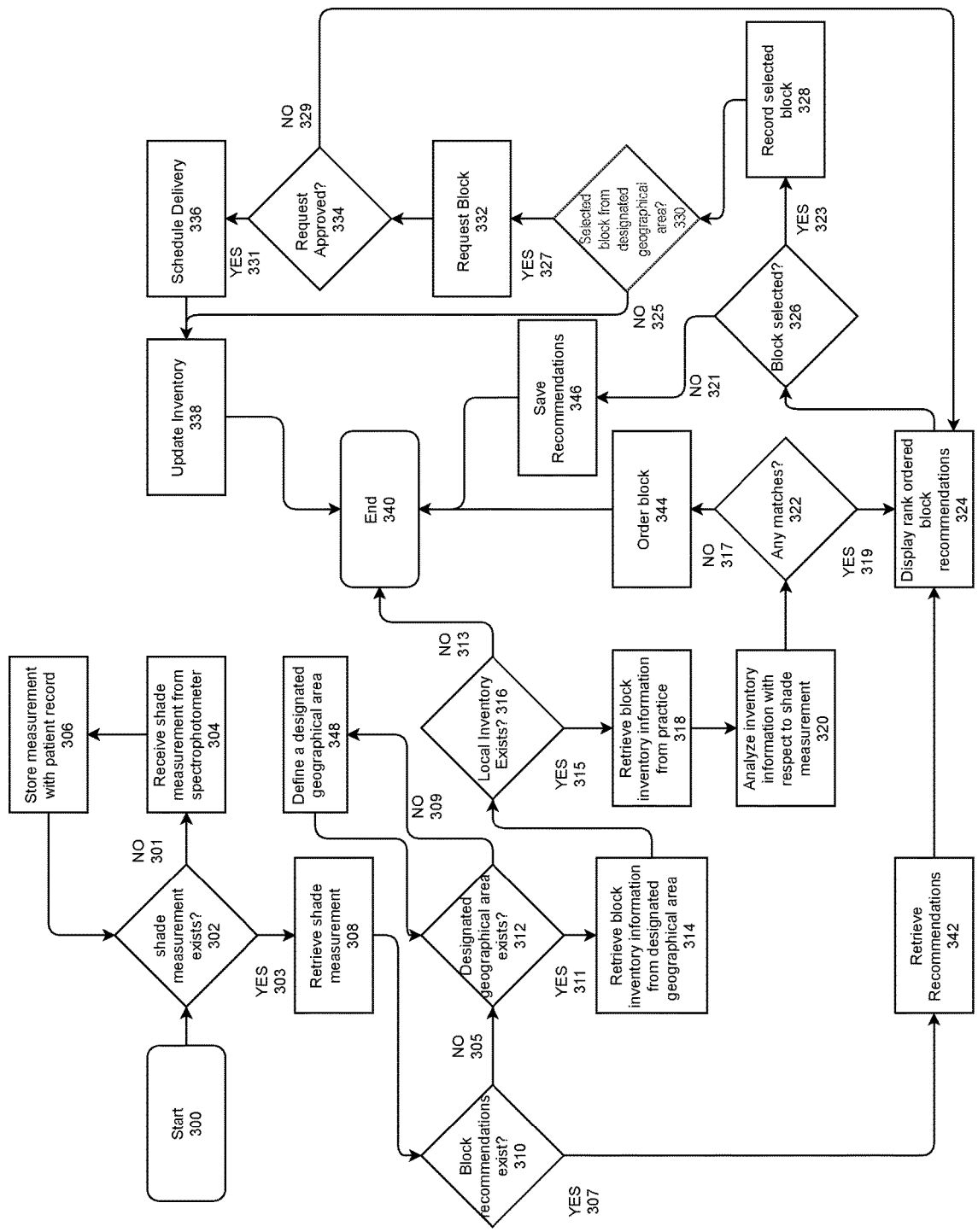
FIG. 3A illustrates a flow chart associated with the operation of the system of shade matching and localized laboratory aesthetics for restorative design in dentistry.

FIG. 3A illustrates a flow chart associated with the operation of the system and method 100. In one embodiment of the present disclosure, the process would typically take place after scanning and modeling the patient's mouth for a particular restoration procedure. After the process is started 300, the system 100 first checks for the existence of a shade measurement for a particular active patient record 302. If no such measurement exists 301, then the dentist operator 204 has the opportunity to work with the patient and spectrophotometer module 218 of the CAD/CAM dentistry system 202 to take the shade measurement. Once the system receives the shade measurement 304, then the system 100 stores the measurement with the patient record 306. In one embodiment, the shade measurement is stored in the patient shade registry 220, but in other embodiments it may be stored in an electronic health record system or the like. Once the shade measurement exists 303, it is retrieved 308 and the system 100 determines if there are any block recommendations for the patient in light of the shade measurement 310.

A block recommendation is a suggested block of material from which the patient's restoration will be milled using the manufacturing device 230 of the CAD/CAM dentistry system 202 based on a shade measurement of the patient. Sample blocks of materials include but are not limited to feldspathic porcelain, ceramic resin hybrid, leucite-reinforced porcelain, lithium disilicate, nano ceramic/resin, composite resin, and zirconia reinforced lithium silicate. One advantage of the system 100 described herein is that the block recommendations are not restricted to just one particular vendor's blocks or system. By capturing the activity and inventory of many systems, it is possible to make the best recommendations in the interest of shade matching for the patient.

If there are block recommendations 307, then the process retrieves the recommendations 342 from the patient registry 220 and displays them in rank order 324, as described below. If there are no existing block recommendations 305, then the system 100 determines if any designated geographical areas exist 312. If not 309, the operator 204, which in some cases is the dentist or a hygienist employed by the practice or any other authorized/designated user of the system, can set up a geographical area from which the dental practice would like to draw dental supplies 348.

If a designated geographical area exists 311, the inventory information from the suppliers in the designated geographical area will be retrieved 314. In some embodiments, the inventory of suppliers in the geographical area may be locally stored on the operator's CAD/CAM system updated periodically (daily, weekly) so as to provide near-real time visibility into inventory. In yet other embodiments, the inventory is queried quickly on-demand to be as accurate as possible. In yet other embodiments, the inventory is queried intelligently based on the type of restoration procedure proposed for the patient. Next, the operator's local inventory is checked 316, i.e. the supplies for which the operator has ordered and taken delivery in their own practice. In one embodiment of the present disclosure, the operator 204 may scan all blocks of material in their inventory with a spectrophotometer module 218 to generate the shade measurement values to be used in the process for making a recommendation 320. In other embodiments, the operator 204 may receive the shade measurement values from the block manufacturer 260 at the time the block is ordered either directly from the block manufacturer 260 or their resellers. In some operator practices, staff may become quite skilled at working with their own stains and glazes with different blocks of material. In this case, they would take spectrophotometry readings of finished blocks and include that in their inventory to further expand the quality of their inventory for making shade recommendations. In some embodiments, cost is included in the inventory information. In other embodiments, the supplier can add a markup to the cost. For example, a dental practice that specializes in restorations may keep a lean supply on hand and may only want to share its inventory with another practice in exchange for a premium. This added cost may be stored in the inventory information. In other embodiments, cost information may reflect the expertise of the supplier in providing characterizations to restorations. In still other embodiments of the present disclosure, if the operator 204 has to return any blocks that were ordered from the block manufacturer 260 or their resellers, then the returned blocks would be removed from inventory along with their corresponding shade measurement values so that those blocks would no longer be considered in the process for recommending blocks 320 for patient restorations.

Once all inventory information has been retrieved 318, it is then analyzed with respect to the shade measurement for the patient 320 to determine if there are any matches 322. In some embodiments, this analysis may also include any characterizations (stains/glazes) for the block that might be necessary for a better match for the patient. If there are no matches in inventory 317, then the operator 204 may be given the opportunity to order the recommended block 344, and the process ends 340. If there are matches 319, then the block recommendations are rank ordered 324. In one embodiment, they are ranked according to the best shade. In another embodiment, they are ranked by cost. In still other embodiments, they are ranked by availability. In further embodiments, they are ranked by estimated delivery time. Other embodiments may combine criteria, such as the next best shade available in the geographical area with a targeted estimated delivery time. Other such rankings may be possible. At this point, the dentist 204 is given the opportunity to select one of the recommendations.

The system then checks to see if a block is selected 326. If not 321, then the block recommendations are saved 346 for later and the process ends 340. In these embodiments, the operator 204 may be wanting to review the recommendations before discussing with the patient, and so it would not be necessary to select a recommendation at that particular time. Please note that saved recommendations may be refreshed by repeating the steps to retrieve inventory from the designated geographical area and/or the practice's own inventory so that recommendations may be current and immediately actionable when the patient is ready to make a selection.

If a block is selected 323, then the block selection is recorded 328. In some embodiments, this selection may be reported to the shade match registry 259 on server device 250. In this respect, one of the advantages of the system and method 100 is that it completes machine learning on a wide scale—creating a map of patient shade measurements and the ultimate blocks selected for their restorations. In other embodiments, the shade match repository 259 can be used in the analysis of block recommendation 320 such that another dimension of the recommendation can be showing the patient what other patients choose for a similar restoration with similarly colored teeth. In yet other embodiments, the system 100 can limit the recommendation of other patients by geography, practice they use, etc. In this respect, the user 204 can tailor a recommendation by other patients in their own same geographical region, for example.

The system 100 then checks to see if the selected block is one from the inventory of the designated geographical area 330. If not 325, then it is selected from the operator's local inventory, and the local inventory is updated 338 and the process ends 340.

If the selected block is one from the inventory of the geographical area 327, then a request 332 for the block is sent to the supplier who has the block in inventory. In some embodiments (discussed later herein), in addition to sending the block, characterization instructions could also be sent with the block to allow the requesting dentist to just order the raw block, but complete the milling and characterizations locally. In some embodiments, for Health Insurance Portability and Accountability Act (HIPAA) compliance, the request is sent with a de-anonymized identifier that can only be linked back to the patient in the operator's CAD/CAM system. This enables the request to be tracked through the supply chain without compromising personal information. In some embodiments, the supplier is given the ability to approve the block 334. If the supplier does not approve 329, then the operator 204 can return to the rank ordered block recommendations 324 and select the next acceptable alternative. If the block request is approved 331, then the system schedules the delivery 336 with the delivery service 240, the inventory is updated 338, and the process ends 340. In some embodiments, the milling time and characterization time can be added into the delivery time (if the milling and/or characterization options are selected) so as to account for any potential time difference associated with manufacturing the block and finalizing the restoration.

In yet another embodiment of the present disclosure, the block request 332 may include a de-anonymized design file for the patient's restoration, such as a stereolithographic file (.STL) or the like. In this respect, it is possible for the supplier to mill the restoration for the operator while waiting for the delivery service 240 to stop by to pick up the block. In some embodiments, the system 100 allows a surcharge to be levied for this service. In this respect, the patient's restoration can be completed faster because the operator 204 is not waiting for the raw block to be picked up and delivered and then milled locally at the operator's practice. In this case, the supplier can mill the block while the delivery service drives to them, resulting in the ability for the operator 204 to instantly install the restoration on the patient when the completed block is delivered. In yet other embodiments, the operator 204 may take a milled block and put it in their local milling machines for additional adjustments before installation in the patient's mouth. In some embodiments, costs associated with the milling would be passed on to the patient and might include: the cost of the block, the cost of an assistant's time for milling the block, cost of delivery. In other embodiments, operators 204 may have separate agreements and or payment frequencies regarding such exchanges. As discussed, characterizations (staining/glazing) may also be part of this manufacturing process.

In still further embodiments, the system could leverage artificial intelligence or machine learning to review the supplies of a given geographical region and proactively suggest times for patients to undergo procedures. For example, a dentist 204 may suggest to a patient that they may need a crown or a bridge. The patient may not need it immediately, but the dentist 204 can color match the tooth for the restoration. The system 100 could then work in the background consulting the suppliers defined in the geographical areas and proactively alert the dentist 204 when the necessary supplies are available or become available.

Figure 3B:
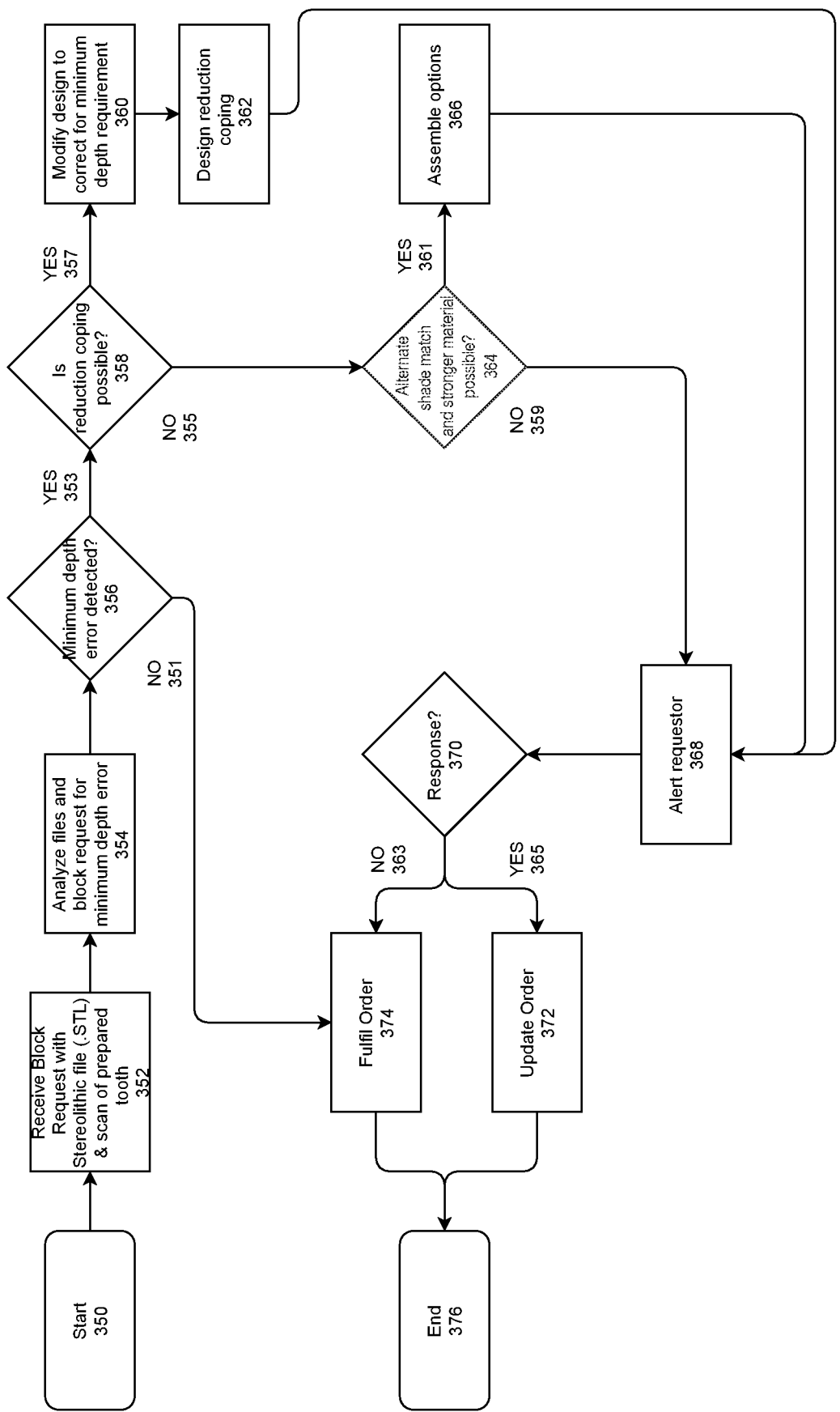
FIG. 3B illustrates a flow chart associated with reduction coping in accordance with embodiments of the present disclosure.

FIG. 3B illustrates a flow chart associated with reduction coping in accordance with embodiments of the present disclosure. CAD/CAM dentistry systems 202 will typically remind dentists 204 of minimal depth requirements as they assemble designs for restorations for their patients with specific types of materials. However, according to embodiments of the present disclosure, it would be possible for the dentist 204 and patient to make a last minute change on material selection (for better shade matching or availability). In the haste of daily work, the dentist 204 may send the design out for milling by a supplier 205[2:N] that has the desired material on hand without re-checking minimum depth requirements. In this case, it would be possible for a milled restoration may be delivered that would ultimately fail the patient. According to embodiments of the present disclosure, it is possible for the supplier 205[2:N] to catch the mistake, give the dentist 204 the opportunity to submit an alternative design before milling, or mill the tooth as designed and provide the necessary reduction coping to ensure the quality of the restoration. In some embodiments, the reduction coping could be farmed out to a lab service 290 if the supplier is unable to perform the work directly.

The process starts 350 with the supplier 205[2:N] receiving the block request from a dentist 204 along with a stereo lithic design file 352 (.STL file). In some embodiments, an anonymized scan of the prepared tooth receiving the restoration will also be sent. The supplier 205[2:N] will analyze the design file, prepared tooth scan, and block request for minimum depth requirements 354 and determine if there is a minimum depth error 356. If no minimum depth error is detected 351, then the supplier 202[2:N] fulfills the order 374 and the process ends 376. If a minimum depth error is detected 353, then the supplier 205[2:N] then determines if reduction coping is possible 358. If it is possible 357, then the supplier 205[2:N] will modify the design file to correct for the minimum depth requirement 360, design a reduction coping 362 (using the scan of the prepared tooth and an acrylic or composite block like a Telio CAD block for CEREC or a cheaper acrylic alternative block or the like), and then alert 368 the requestor 204 and await for a response 370 from the requestor 204. If the dentist 204 approves the modification to the design 365, then the order is updated 372 and the process ends 376. In some embodiments, updating the order involves milling the new design modified for the minimum depth requirement and generating the corresponding reduction coping for the new design. In some embodiments, the reduction coping may be farmed out to a lab service 290 and coordinated for delivery to the dentist 204 at the same time as the milled restoration, either independently or together. If the dentist 204 does not approve the modification to the design 363 within a specified timeframe, then the original order will be fulfilled as requested 374, and the dentist 204 and patient can take the risk that the restoration will function properly without meeting the minimum depth requirement, and the process ends 376. In some embodiments, both the original and the modified design are supplied to the requesting dentist (additional fees may be incurred). In still further embodiments, settings in the software could indicate a preference of the requesting dentist to always receive modified designs if problems are detected, always receive the original design, or some combination therein based on factors such as the time deadline for the restoration, the cost of the blocks or the like.

If reduction coping is not possible 355, then a determination 364 is made as to whether or not there are stronger materials available that would ensure that the existing design would work. Shade matching would also be part of this evaluation. If no alternatives exist 359, then the requestor 204 is alerted 368 and a brief delay awaiting a response 370. This would allow the dentist 204 to cancel the order or submit a modified design that rectifies the minimum depth requirement. If the dentist 204 does not respond within a given time period, then the original order will be fulfilled as requested 374, and the dentist 204 and patient can take the risk that the restoration will function properly without meeting the minimum depth requirement, and the process ends 376.

If alternatives do exist 361, then options will be assembled 366 (different materials, different shades, costs, etc.). For example, it could be determined that selecting a stronger material would allow the existing restoration design to work unmodified, but it would involve a tradeoff with a less accurate shade match than the material originally requested and/or additional characterizations. After alternatives are identified, the requester 204 is alerted 368 and there is a brief delay while waiting for a response 370. If the dentist 204 selects one of the alternative options (either independently or after consultation with the patient) 365, then the order is updated 372 and the process ends 376. In some embodiments, updating the order involves milling the design with the alternative materials that were recommended. If the dentist does not approve one of the alternative options 363 within a specified timeframe, then the original order will be fulfilled as requested 374, and the process ends 376. Again, in some embodiments, preferences and time thresholds could be set by the dentist. For example, the dentist could specify that if no response is given within 15 minutes of a notification of an alternative design, then automatically fulfil the order with the modified design, or make both restorations, or just make the original design, or call the office and wait for a definitive response.

FIG. 3C illustrates a flow chart associated with the machine learning process of the system of shade matching and localized laboratory aesthetics for restorative design in dentistry. In one embodiment, the process starts 378 when triggered by the system such as when analyzing inventory information with respect to shade measurement 320. The stereo lithic design file and a scan of the prepared tooth are received 380 which may also include shade measurements associated with the design file and the restoration procedure planned. An analysis is then completed 382 using artificial intelligence initialized with other stereo lithic designs, scans, and shade measurements. A check is made 384 to see If any design suggestions can be made. If yes 385, then the design suggestions are returned 386, and the process ends 390. Suggestions may be partial. For example, in some cases, it may be possible to make a block recommendation but no characterization instructions might be recommended. If no suggestions can be made 383, then no suggestions are confirmed 388 and the process ends 390.

FIG. 4A illustrates a user interface 400 under one embodiment of the present disclosure for defining the designated geographical area 401. In one embodiment of the disclosure, the designated geographical area may include specific dental practices in the local community for which the dentist has a personal relationship (405, 423). In other embodiments, the dentist can define a rule, for example all dental practices in a 10 mile radius from the dentist's practice (412, 413, 414, 415,419, 420). FIG. 4B illustrates and example of this embodiment with a map 470 showing the dental practice 204 surrounded by geographical areas defined as a certain radius from the dental practice with some suppliers 205 remaining in the designated area 471 and others falling in non-designated areas 472. In this respect, the dentist 204 does not need to have a relationship with the practice or even know beforehand if they carry any supplies that would be needed. The system 100 can query from those other practices that are enrolled in the system to assist the dentist 204 in identifying the supplies needed. In additional embodiments, if the radius from the dentist's practice do not produce any results, the system 100 can automatically expand beyond the given geographical parameters (i.e. go out a further distance) until a search result can be found. For example, the system 100 could progressively expand the search an additional 5 miles out until a practice with the supplies needed is found. Supplies further out would obviously be more expensive to deliver on-demand, but in some embodiments, the system 100 could adjust the pricing accordingly or supplying dentists could establish standard pricing rules based on distances. In other embodiments, the designated geographical area may be filtered to identify only practices that are known to have similar CAD/CAM systems 202 to the one used by the dentist (411, 422, 424). In another embodiment, the system 100 can either self-identify the operator's CAD/CAM system or provide a choice of common systems 445. In yet other embodiments, the designated geographical area may include dental suppliers in the area, not just dental practices, who might have the needed supplies on hand (407, 408). In other embodiments, the designated geographical area may be defined to only include those practices with a positive rating of participating in the system 100 (406,444, 425). In other embodiments, the designated geographical area may include information that estimates the delivery times from the participating supplier/dental practice to the practice of the operator (410, 446). In other embodiments, a variety of search and filter functions are provided to the provider to offer maximum flexibility in defining the designated geographical area. Mechanisms for executing the search 416 and clearing attributes 417 may also be provided. A variety of pagination controls 443 may be provided for working through the search results 418.

Figure 5:
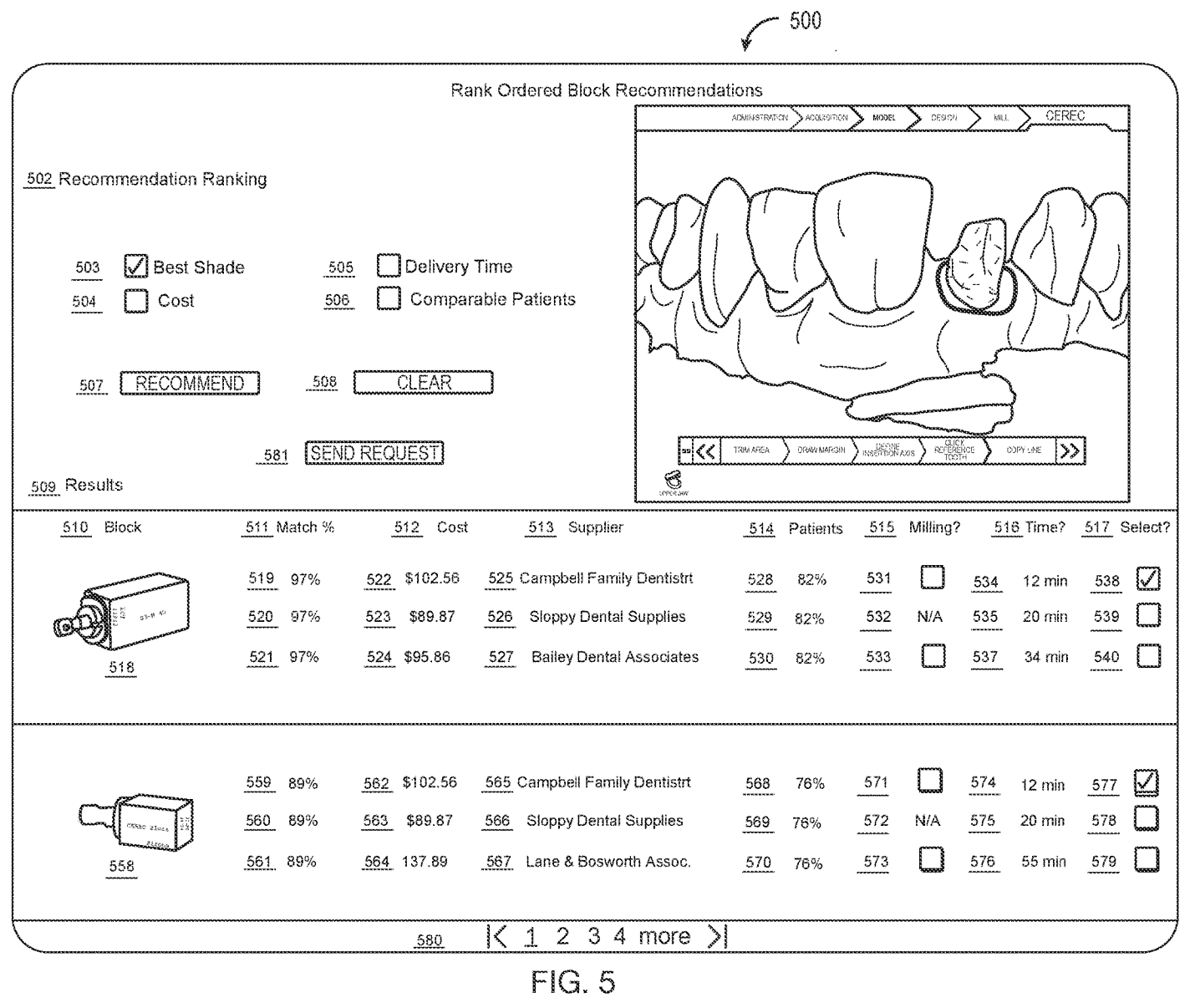

FIG. 5 illustrates an exemplary user interface 500 under one embodiment of the present disclosure for rank ordering, selecting, and ordering inventory. In one embodiment of the disclosure, the dentist/operator 204 can select from different attributes (503, 504, 505, 506) for ranking the recommendations 502. In one embodiment, the dentist can select best shade 503, meaning the shade that most closely matches that of the patient's tooth, as taken by the spectrophotometer module 218. In another embodiment, the rank can be by the cost of the block to the patient 504 or the cost to the practice or some combination therein. In still other embodiments, the ranking can be done by delivery time 505, meaning how long it would take for the necessary block to be retrieved from inventory (either locally or from a supplier/dental firm in the geographic area). In some embodiments, this may also include milling time and/or characterization time (either separately designated or together). In still further embodiments (not shown) block recommendations would be sorted by the availability of the supplier to complete the characterizations. In additional embodiments, ranking may be by comparable patients 506, meaning the recommendations are based on what patients with comparable shade measurements end up selecting. In some embodiments, these attributes are mutually exclusive (meaning the dentist can only choose one). In other embodiments (not shown) it is possible for the dentist to weight these attributes so as to affect the results involving all attributes. In some embodiments (not shown), it is possible for a dentist 204 to create a white list or a list of preferred or favorite suppliers 205[2:N] or a black list of suppliers 205[2:N] for which the dentist does not want to interact.

The user interface 500 includes operational buttons for clearing the attribute selections 508 and getting the recommendations 507. It also includes a button 581 for sending the request for an inventory block once one is selected (see 538,539,540,577,578,579).

The exemplary interface 500 shows the recommendation results 509. In this case, it shows the block recommended (510, 518, 558). In some embodiments, the interface shows the degree to which the block recommended (510, 518, 558) is a match for the current patient based on their shade measurements (511,519,520,521,559,560,561). As shown, the first block 518 is a 97% (519,520,521) match for the patient whereas the second block 558 is a 89% (559,560, 561) match for the patient.

In some embodiments, the cost is shown (512, 522, 523, 524, 562, 563, 564) for the dentist to optionally share with the patient. In further embodiments, this cost could include just the raw inventory cost, a premium (applied from the supplier), and even still the cost from the delivery service and any premium applied (given the time of day of the expected request). In other embodiments, these costs could also reflect any coverage by the patient's insurance company.

In additional embodiments, the supplier (513,525,526, 527,565,566,567) is identified. While not shown, in some embodiments, it would be possible for the dentist to click on the supplier and find attributes about the supplier.

In additional embodiments, the interface 500 could show the comparables from patients with similar shade match readings (514,528,529,530,568,569,570). In this example, the patient can see that the first recommended block 518 is selected by 82% of patients with similar shade measurements (528,529,530), as recorded and reported by the system 100 (obviously, the more users of the system 100, the greater the confidence the patient would have with this metric). Similarly, for the second recommended block 558, only 76% of patents make this selection when faced with similar shade readings (568,569,570).

In yet other embodiments, the interface 500 shows that the dentist 204 can be presented with an option (515) to have the supplier 205 [N:2] mill the block for them based on their design, provided the supplier supports this feature (531,532, 533,571,572,573).

In still other embodiments, the interface 500 shows the dentist the delivery time 516 for the block based on supplier (534,535,536,574,575,576). Note that in some embodiments, the time can be adjusted based on whether or not the supplier will be asked to mill the block vs just delivering the raw inventory part.

Obviously, there could be many recommendations, and so the interface 500 would have some way to navigate additional results not immediately visible on the interface by some pagination mechanism (580). In some embodiments, the block recommendations can differentiate between just a block match and a degree to which the characterizations are also needed for a match and patient satisfaction. This would give the dentist greater knowledge and flexibility, i.e. I can get this block, but for best results we would want the supplier to do the characterizations. Once the dentist 204 and patient have decided on a recommendation, they can indicate their selection 517 through the interface 500. In some embodiments, the system 100 can enforce only one block selection. In other embodiments, the dentist 204 could order multiple recommendations, if they know they have a client that may change their mind—it may be more cost and time efficient to order the restoration in multiple blocks rather than have to delay the procedure if the patient decides against the initial selection once it is received.

Figure 6A:
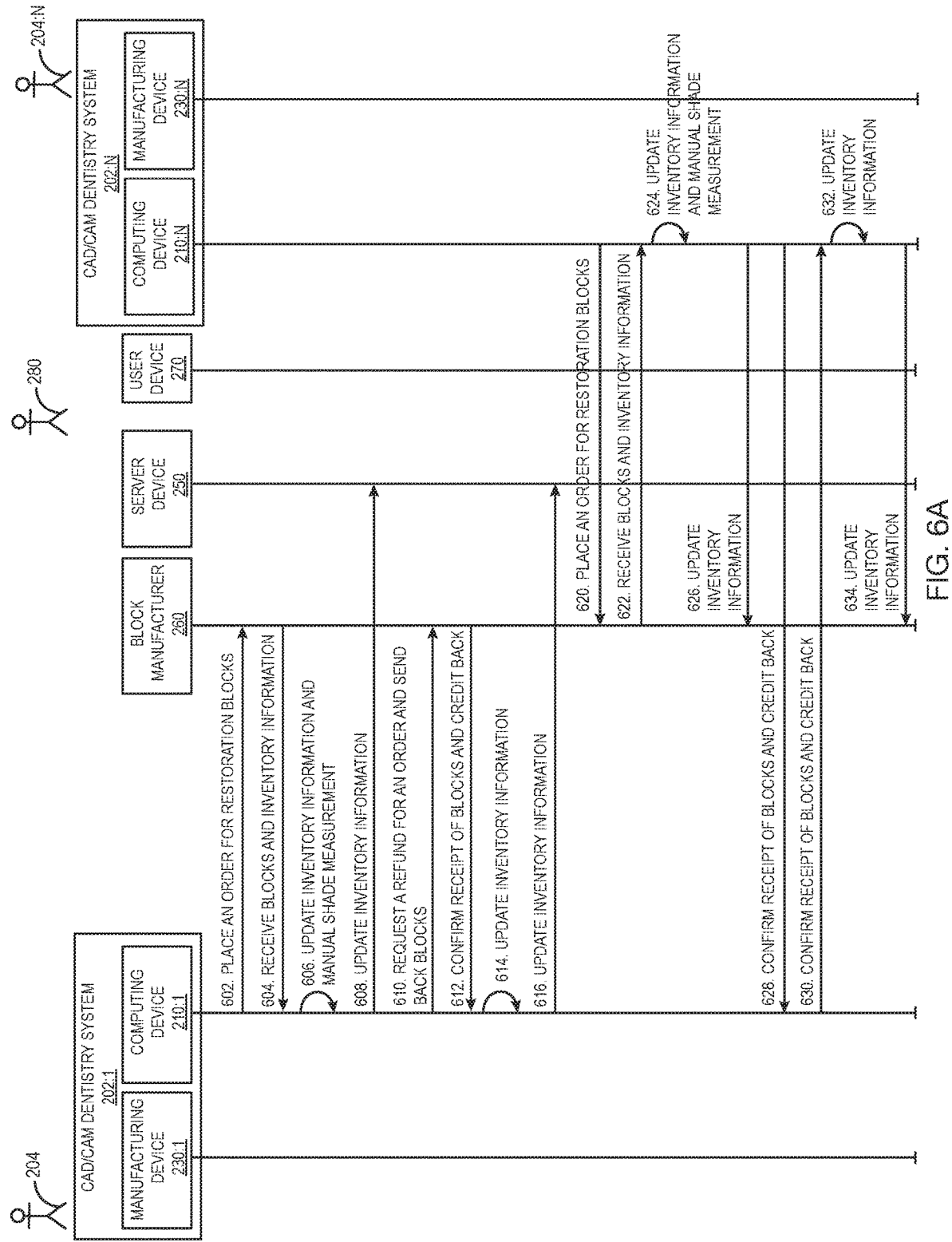
FIG. 6A illustrates a network flow diagram related to inventory management according to embodiments of the present disclosure.

FIG. 6A illustrates a network flow diagram related to inventory management according to embodiments of the present disclosure. A dentist 204 can place an order 602 for restoration blocks from the block manufacturer or reseller 260. This could be done from the computing device 210 using either the custom software installed along with the manufacturing device 230 or a simple web browser on another computer in the office or a mobile phone or tablet. The dentist 204 then receives 604 the blocks and inventory information from the manufacturer 260. In some embodiments, the inventory information is just sent in a traditional packing slip. In other embodiments, the inventory information is available through an account online with the manufacturer and accessible from either a web browser or the integrated software installed with the manufacturing device 230. In other embodiments, the inventory information is available through a web service application programming interface (API) such as Extensible Markup Language (XML), JavaScript Object Notation (JSON), and the like. The dentist 204 can then update 606 his local inventory information 22202 and also take shade measurements of the inventory using the same spectrophotometer module 218 that would be used with patients. In some embodiments, a dentist 204 may have multiple spectrophotometers 134 and would not need to use the same device on a patient that would be used with the order of restoration blocks. The system 100 would then update 608 the inventory information in the server device 250 in the user inventory 25704. In some embodiments, this is done using the receipt of new inventory as the trigger. In other embodiments, the syncing of inventory is done on a periodic basis. In other embodiments, it is a combination of triggers (like new orders, using inventory on patients) and periodic polling (such as daily or weekly). In some embodiments (not shown) the block manufacturer 260 would be able to communicate the inventory information for new orders and returns directly to the server device 250 on behalf of the dentist 204.

If there is a mistake with the order and the dentist 204 needs to request a refund and send back inventory for some reason, then the process reverses. The dentist 204 requests a refund 610 and sends the blocks back. The manufacturer 250 confirms receipt of the blocks 612 and gives the appropriate credits back. The local inventory 22202 is updated 614 and then the server device 250 and user inventory 25704 is updated 616 to reflect the inventory changes. In some embodiments, the local inventory 22202 can be updated independent of any credit received (i.e., once the dentist 204 sends the blocks back, they would not be in local inventory 22202 for either the dentist to use or to share with other practices 205[2:N]). Steps 620, 622, 624, 624, 626, 628, 630, 632, and 634 reflect a similar process for other practices 205[2:N] that may be going on asynchronously for those practices.

Figure 6B:
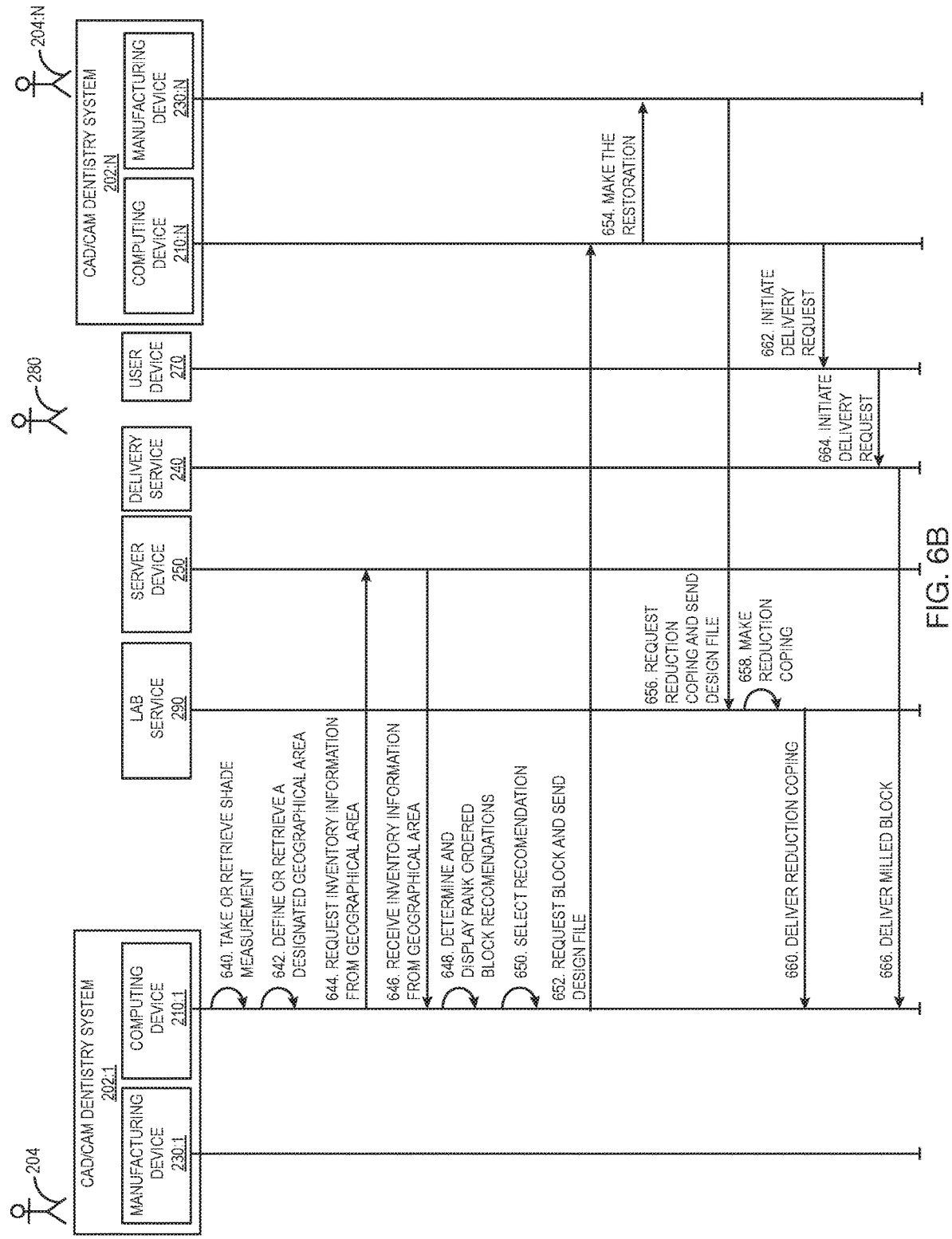
FIG. 6B illustrates a network flow diagram related to inventory exchange according to embodiments of the present disclosure.

FIG. 6B illustrates a network flow diagram related to inventory exchange according to embodiments of the present disclosure. Computing device 210 takes or retrieves 640 a shade readings 22006 for a patient. The dentist 204 defines or retrieves 642 a designated geographic area 22108. In some embodiments, the designated geographic area is selected using an interface similar to that shown in FIG. 4. The computing device 210 requests 644 user inventory information 25704 from the server device 250 according to users in the geographic area requested. The computing device 210 then receives 646 the user inventory information from server device 250. In some embodiments, this inventory information is cached in remote inventory 22222. The patient shade information and the block inventory from the geographic area are then analyzed 648 to determine and display a rank order of block recommendations. In some embodiments, the rank order of blocks is displayed using an interface similar to FIG. 5. In some embodiments, this analysis is performed on the computing device 210. In other embodiments, this analysis is performed on the server device 250. In still other embodiments, the analysis is performed by both the computing device 210 and server device 250. In some embodiments, the analysis comprises comparing the component measurements (chroma, hue, value) of the shade measurement of the patient to the corresponding components of the shade for the block candidate. In other embodiments, a single measurement that captures the component information may be used. The dentist then selects 650 a recommendation. The dentist 204 can select a block 652 using the computing device 210 and send the design file to the supplier 202[2:N]. In some embodiments, the information transmission is facilitated by the server device 250 and the request registry 258. The supplier 202[2:N] makes 654 the restoration using the design file. In some embodiments, the supplier 202[2:N] requests 656 reduction coping and sends the design details to a lab services 290. In some embodiments, the supplier 205[2:N] may be able to provide the reduction coping directly (so they act as the lab service). The lab service 290 then makes 658 the reduction coping and coordinates the delivery to the dentist 204. In some embodiments, the supplier 205[2:N] may receive the reduction coping so that it may be sent with the final milled restoration as well. The supplier 205[2:N] initiates 660 the delivery request. In some embodiments, the computing device 210 sends the relevant details to a user device 270 which then initiates 662 the delivery request with the delivery service 240. The delivery service 240 then delivers 664 the final milled restoration to the dentist 204.

Figure 6C:
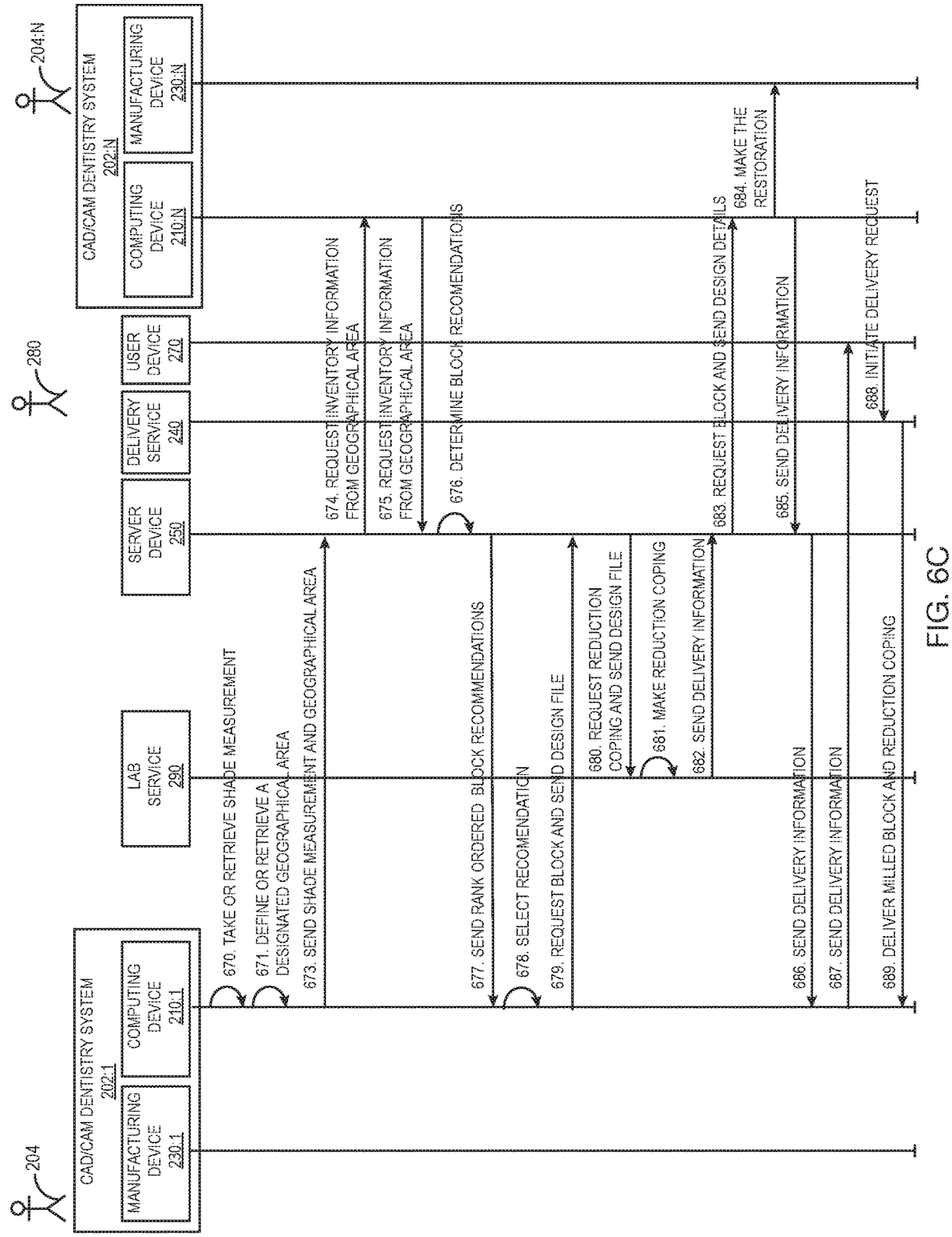
FIG. 6C illustrates a network flow diagram related to inventory exchange according to embodiments of the present disclosure.

FIG. 6C illustrates a network flow diagram related to inventory exchange according to embodiments of the present disclosure. Computing device 210 takes or retrieves 670 a shade reading 22006 for a patient. The dentist 204 defines or retrieves 671 a designated geographic area 22108. In some embodiments, the designated geographic area is selected using an interface similar to that shown in FIG. 4. The computing device 210 sends the shade measurement and geographic area 673 to the server device 250. The server device 250 requests 674 and receives 675 user inventory information 25704 from the other computing devices 210 [2:N] according to users in the geographic area requested. In some embodiments, this inventory information is cached in remote inventory 22222. The patient shade information and the block inventory from the geographic area are then analyzed to determine 676 and send 677 a rank order of block recommendations to the computing device 210. In some embodiments, the analysis comprises comparing the component measurements (chroma, hue, value) of the shade measurement of the patient to the corresponding components of the shade for the block candidate. In other embodiments, a single measurement that captures the component information may be used. The dentist then selects 678 a recommendation. The dentist 204 the requests the block using the computing device 210 and sends 679 the design file to the server device 250. In some embodiments, the request and design file are stored in the request registry 258. In some embodiments, the server device 250 does quality control on the request. In some embodiments, the quality control can include making sure the design file does not have any information that would compromise the identity of the patient or the requesting dentist 204 or run afoul of any HIPAA regulations. In other embodiments, the server device 250 can catch reduction coping errors and request 680 reduction coping and sends the design details to a lab services 290. The lab service 290 then makes 681 the reduction coping and sends the delivery information to the server device 250. Concurrently or serially (depending on if the server device can determine delivery time differentials between milling the restoration and generating the reduction coping), the server device 250 requests the block and sends the design file 683 to the supplier 202[2:N]. The supplier 202[2:N] makes 684 the restoration using the design file and sends delivery information 685 to the server device 250. The server device 250 then sends the delivery information 685 to the requesting dentist 204. In some embodiments, the delivery information is simply information indicating that the order is now complete. In other embodiments, the delivery information may include information to automatically schedule the delivery with one or more preferred delivery services pre-selected by the requesting dentist 204. The requesting dentist 204 can then use computing device 210 to send 686 the delivery information to a user device 270 from which a delivery request 687 can be initiated with the delivery service 240 which then delivers 688 the milled block along with the reduction coping. In this respect, it is possible for the requesting dentist 204 who is normally working in the system on their CAD/CAM software on computing device 210 to be notified when the order is complete, easily transfer the information to a mobile device in the office which can then use one of many standard delivery services to pick up the restoration and reduction coping and have them delivered to the office.

Figure 6D:
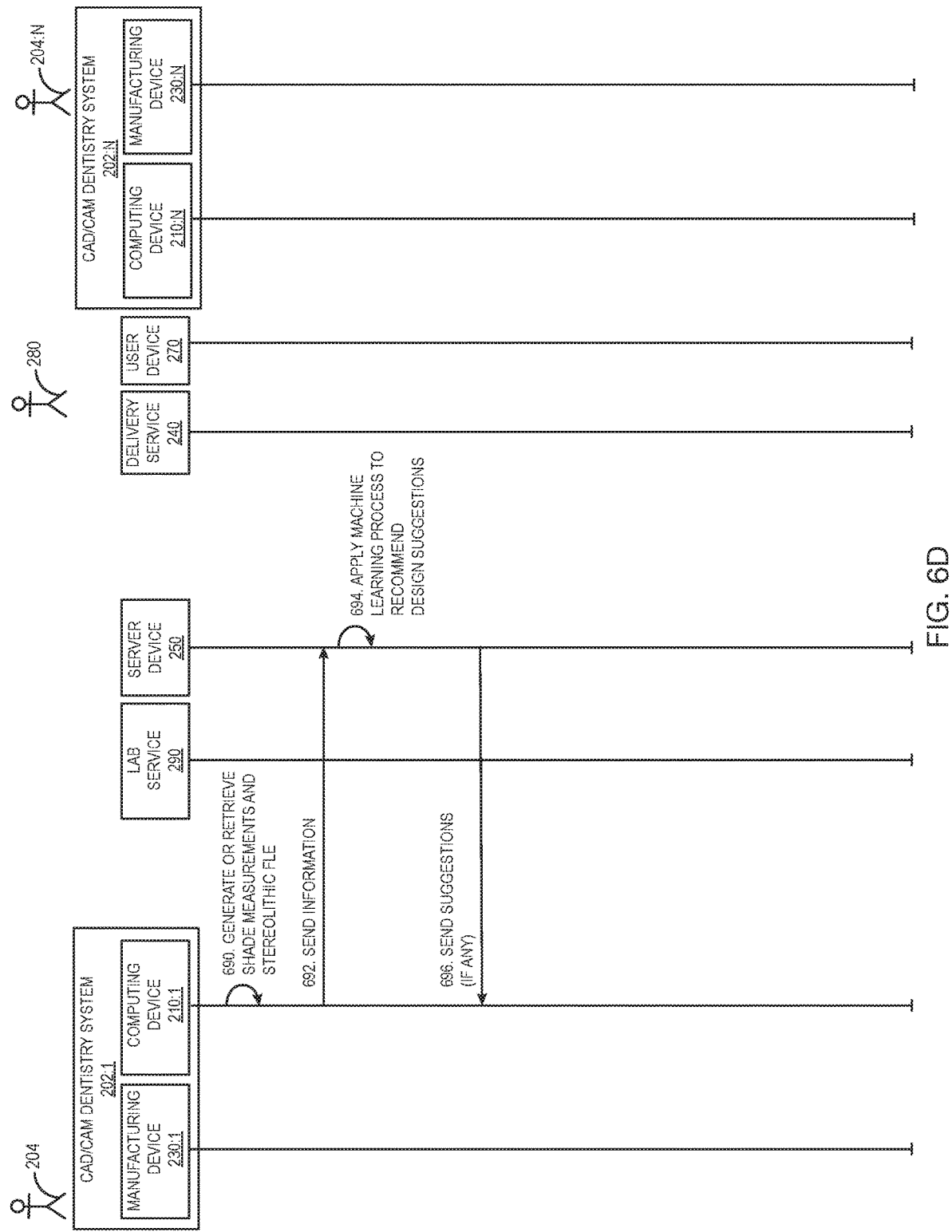
FIG. 6D illustrates a network flow diagram related to the machine learning process of the system of shade matching and localized laboratory aesthetics for restorative design in dentistry.

FIG. 6D illustrates a network flow diagram related to the machine learning process of the system of shade matching and localized laboratory aesthetics for restorative design in dentistry. Computing device 210 generates or retrieves 690 a shade reading 22006 and a stereo lithic design file 22008 for a patient and optionally a scan of the tooth. It then sends this information 692 to the service device 250 which applies a machine learning process 694 to make recommendations. These recommendations may include suggestions on improving the design of the restoration itself or staining/glazing recommendations for how to best match the shade of the restoration for the patient. The server device 250 then sends the suggestions 696 back to the computing device 210.

FIGS. 6E-6K illustrates an example of augmented reality applied to the staining and glazing step of the system of shade matching and localized laboratory aesthetics for restorative design in dentistry. In this respect, the system is not only able to supply a block recommendation but also characterization instructions for best results if the dentist has to do the staining/glazing at the practice (instead of ordering a completed restoration from the supplier). A representative restoration 6102 is shown. This particular restoration is for a crown (shown in plan view 6106 and profile view 6104), but it could be any restoration (implant, bridge, etc.). According to embodiments of the present disclosure, after users 204 of the system contribute information to the system, such as initial designs, shade readings, and final products (22006 and 22008), the system has developed a library of information that can be leveraged by machine learning processes to generate recommendations for new users of the system (FIG. 6D). FIGS. 6E-6K show an examples staining/glazing recommendation 6118 (with an embodiment artistic rendering of how this might look like in 6119). In some embodiment, the recommendation would include a pattern 6110 for applying a light brown stain into the grooves of the restoration 6102. In further embodiments, there may be recommendation of white stains 6112 on the perimeter of the restoration to define the occlusal table, including some white stains on the cusp ridges. In additional embodiments, the recommendation might include a violet stain 6114 to further define the occlusal table. Still further embodiments would involve a recommendation 6116 with a guide for blue staining across the cusp tips. Depending on the nature of the restoration and the desired shade, additional recommendations of stains/glazes would be made.

In some embodiments of the present disclosure, the entire recommendation 6118 could be revealed to the user 204 using an augmented reality system. In one embodiment, this augmented reality system would be embodied as an application 6124 on a smart phone 270 that could optionally be put in a cradle 6120 for hands-free use. In some embodiments, it may be necessary to do some calibration of the augmented reality system. But once calibrated properly, the augmented reality system would allow the user 204 to hold the restoration 6102 on a hook 6122 (or similar) behind the phone and allow the camera in the phone to work with the application 6124 to display the recommendation 6118 (either in stages or in entirety) on the image so that the user could determine exactly where and how to apply the stains from the recommendations and in what order. In still further embodiments, the augmented reality system could include the ability to detect when a user 204 has applied the recommended staining patter to trigger them to move on to the next stage. In this respect, the system 100 would ameliorate the possibility that the user 204 would forget their place in completing the staining/glazing step. In still further embodiments, the augmented reality system may be able to take dynamic shade measurements of the applied stains and glazes to further instruct the user of when they have applied non-optimal amounts of staining so that they could adjust accordingly (either add more or thin out what they have already applied). In still other embodiments, the wand of the CAD/CAM dentistry system could be employed for the augmented reality system. In an embodiment where the wand contains a camera and spectrophotometer and the augmented reality system is built into the CAD/CAM system application itself, the user could place the wand in a hands-free cradle and similarly get recommendations overlaid onto restoration in real time as the user applies the staining and glazing. In still other embodiments, the augmented reality system could be distributed in real time so as to allow an active consult on a particular restoration. In this embodiment, users of the same CAD/CAM dentistry system could interact via teleconferencing software (either embedded in the CAD/CAM dentistry application or independent of it) so that one user 204 could observe the recommendations and staining/glazing activities of the other users and provide professional advice on improving or understanding the recommendations. In yet further embodiments, the same system could be used to provide recommendations and instructions for re-staining/re-glazing existing restorations whose color has faded over time through use by the patient. While this representative embodiment focused on staining on the top of a crown, similar recommendations could be given on the side of the restoration as well, and the embodiments described herein should not be considered exclusive of these additional embodiments. In still further embodiments, the system 100 could connect the user 204 of the augmented reality system in an ad-hoc manner to a technician at the lab service 290 or other supplier 205 to provide staining and characterization guidance to the user 204 in near real-time. In this embodiment, instead of getting machine learning recommendations on staining/glazing, the user 204 would get specific advice on their actual restoration from a lab technician equipped with a real-time view of the restoration (for example through a mobile device 270 or computing device 210) and the shade readings that the user 204 took for the patient as well as any other detailed information about the design that would enable the lab technician to supply expert advice on shade matching the restoration. The technician (290,205) could use touchscreens on a mobile phone or tablet to identify multiple areas where the user 204 should apply different stains and glazes, and they would appear (similar to 6118) in near real-time on user's screen much like what is shown in FIG. 6K. These interactive sessions could further be fed back into the machine learning processes to further improve the system. Interactive sessions like this would be invaluable in pandemic situations (like COVID-19) where the dentist is able to operate in a limited capacity to continue to make restorations for patients (because of onsite CAD/CAM equipment) but loses the ability to send the restoration to the lab for proper characterization. In some embodiments, network presence and availability of both the dentist 204 and the lab technician at the lab service 290 could be tracked to provide an immediate time for them to do an interactive staining/glazing session, or to schedule a time that is convenient for both. In other embodiments, the staining could be asynchronous, where the technician gets the design file and shade measurements and designs a custom map (similar to FIG. 6J) for staining for the dentist 204 to pick up at a time that is convenient. In still additional embodiments, the augmented reality system is embedded in or works in conjunction with standard video conferencing software (Zoom and the like). Other embodiments would involve simulation software for the augmented reality software that would take a staining/glazing design (either generated by machine learning or via a lab technician in near real-time or asynchronously) and would render that the staining pattern would look like if completed and processed (heated in a SpeedFire oven) to allow the dentist 204 and patient to see what the stained restoration would look like. Again, this simulated final product could be generated with the help of machine learning applied to the system 100 that collects shade readings, designs, and then captures images of the final restoration that is put in place.

In still further embodiments, the process of milling the restoration via the CAD/CAM system 202 would include a step whereby the restoration is physically marked so as to indicate what types of characterizations should be included on the restoration and where. In some embodiments, there is a legend of line types (solid, dashed, dotted, etc.) and line weights (widths) that could convey the different types of stains and glazes to use. In some embodiments, these markings might be applied to the restoration with temporary ink or permanent ink that would not affect the shade of the restoration after the restoration has been stained and glazed and processed in the kiln. In other embodiments, the markings could be slight engravings on the restoration that would be invisible to the patient after the staining/glazing process was complete.

Figure 7:
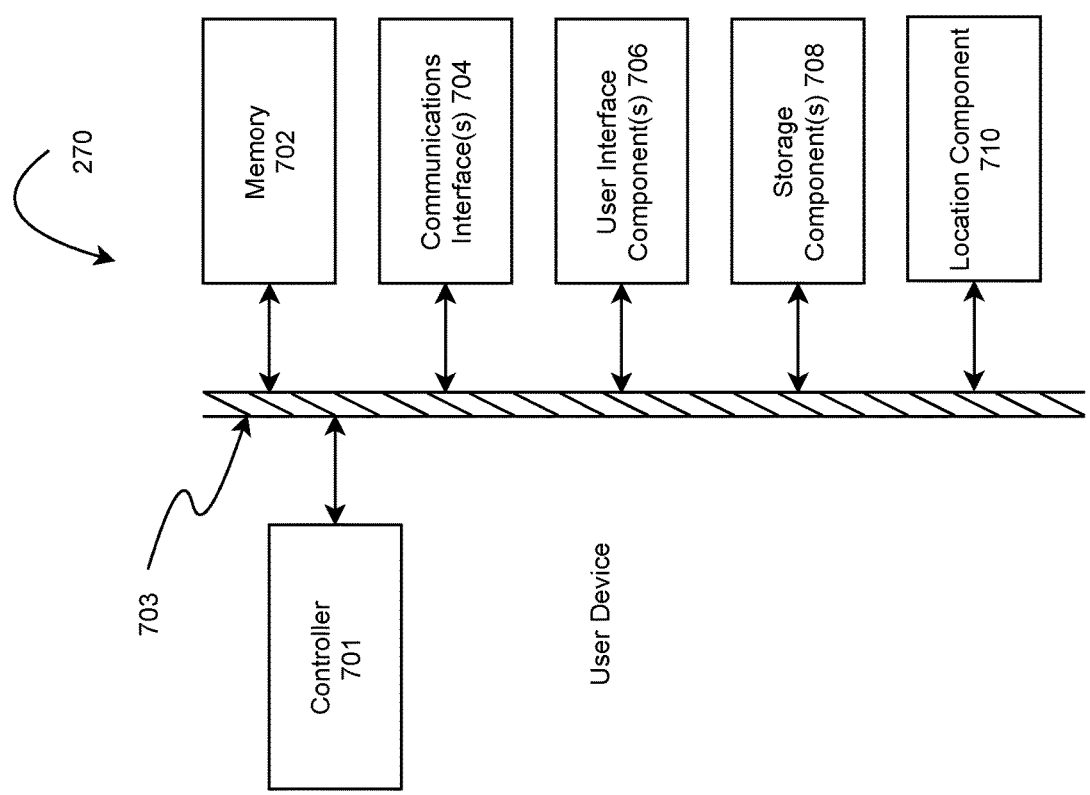
FIG. 7 is a block diagram of a user device 270 according to one embodiment of the present disclosure.

FIG. 7 is a block diagram of a user device 270 according to one embodiment of the present disclosure. As illustrated, the user device 270 includes a controller 701 connected to memory 702, one or more communications interfaces 704, one or more user interface components 706, one or more storage components 708, and a location component 710 by a bus 703 or similar mechanism. The controller 701 is a microprocessor, digital application specific integrated circuit (ASIC), field programmable gate array (FPGA), or the like. In general, the user device 270 includes a control system 271 having associated memory 702. In this embodiment, the controller 701 is a microprocessor, and the user interface (UI) module 272, communications module 273, and configuration module 274, and location module 275 are implemented in software and stored in the memory 702 for execution by the controller 701. However, the present disclosure is not limited thereto. The aforementioned functions and module may be implemented in software, hardware, or a combination thereof. The user device 270 also includes a communication interface 704 enabling the user device 270 to connect to the network 208. The one or more user interface components 706 include, for example, a touchscreen, a display, one or more user input components (e.g., a keypad), a speaker, or the like, or any combination thereof. The storage component(s) 708 is a non-volatile memory. In this embodiment, the location component 710 is a hardware component, such as a GPS receiver. However, the present disclosure is not limited thereto.

Figure 8:
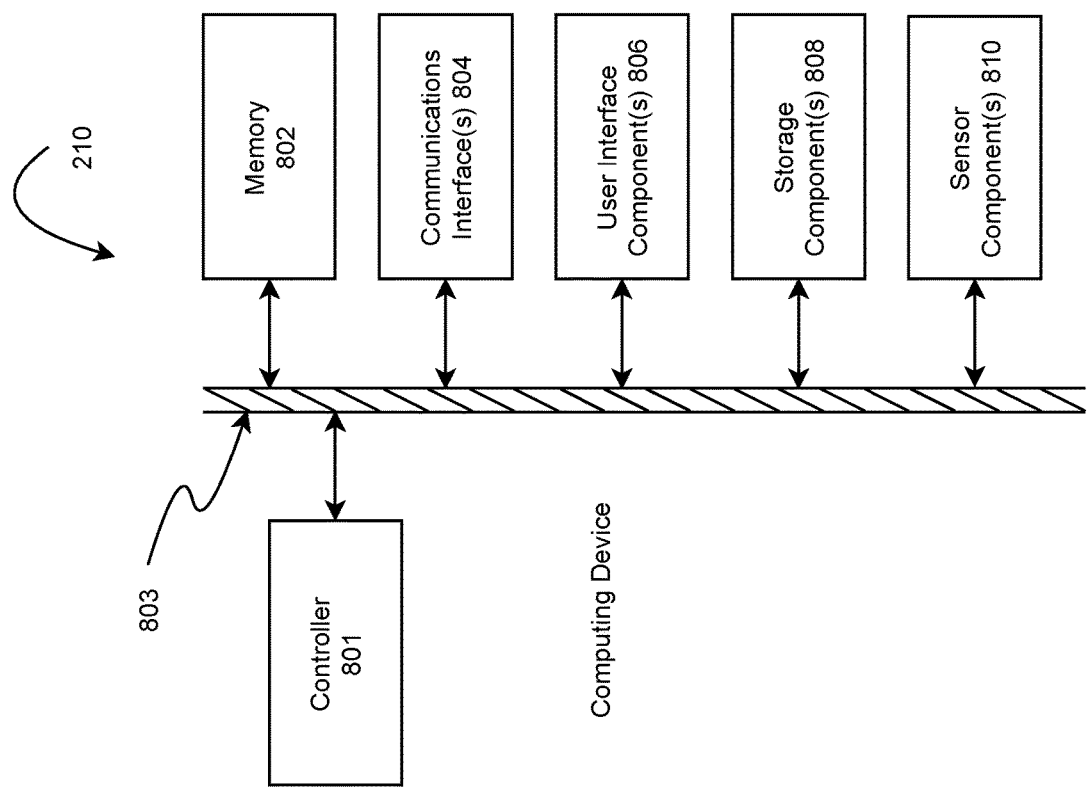
FIG. 8 is a block diagram of a computing device 210 according to one embodiment of the present disclosure.

FIG. 8 is a block diagram of a computing device 210 according to one embodiment of the present disclosure. As illustrated, the computing device 210 includes a controller 801 connected to memory 802, one or more communications interfaces 804, one or more user interface components 806, one or more storage components 808, and a sensor component 810 by a bus 803 or similar mechanism. The controller 801 is a microprocessor, digital ASIC, FPGA, or the like. In general, the computing device 210 includes a control system 211 having associated memory 802. In the controller 801 is a microprocessor, and the display module 212, user interface module 213, communications module 214, power management module 215, capture module 216, storage module 217, spectrophotometer module 218, and inventory module 219 are implemented in software and stored in the memory 802 for execution by the controller 801. However, the present disclosure is not limited thereto. The aforementioned functions and module may be implemented in software, hardware, or a combination thereof. The computing device 210 also includes a communication interface 804 enabling the computing device 210 to connect to the network 208 and to the manufacturing device 230. The one or more user interface components 806 include, for example, a touchscreen, a display, one or more user input components (e.g., a keypad), a speaker, or the like, or any combination thereof. The storage component(s) 808 is a non-volatile memory. In this embodiment, the sensor component 810 is a hardware component, such as a camera wand. However, the present disclosure is not limited thereto. Note, while not shown, it is possible for the computing device 210 to have its location defined by software (such as by using an IP address range) or by an optional hardware component (like a GPS receiver). In some embodiments, computing device 210 operates in a trusted computing environment under the technology and standards developed by the Trusted Computing Group.

Figure 9:
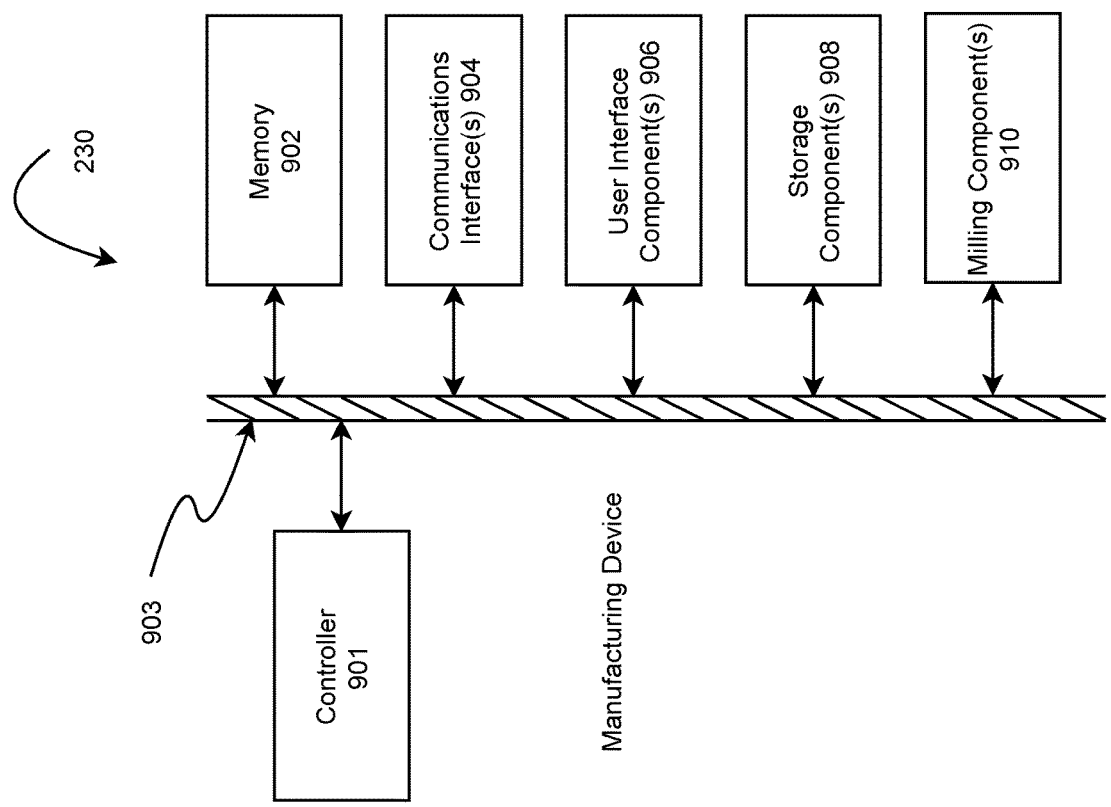
FIG. 9 is a block diagram of a manufacturing device 230 according to one embodiment of the present disclosure.

FIG. 9 is a block diagram of a manufacturing device 230 according to one embodiment of the present disclosure. As illustrated, the manufacturing device 230 includes a controller 901 connected to memory 902, one or more communications interfaces 904, one or more user interface components 906, one or more storage components 908, and a milling component 910 by a bus 903 or similar mechanism. The controller 901 is a microprocessor, digital ASIC, FPGA, or the like. In general, the manufacturing device 230 includes a control system 231 having associated memory 902. In this embodiment, the controller 901 is a microprocessor, and the display module 232, user interface module 233, communications module 234, power management module 235, manufacturing module 236, and storage module 237 are implemented in software and stored in the memory 902 for execution by the controller 901. However, the present disclosure is not limited thereto. The aforementioned functions and module may be implemented in software, hardware, or a combination thereof. The manufacturing device 230 also includes a communication interface 904 enabling the manufacturing device 230 to connect to the network 208 and to the computing device 210. The one or more user interface components 906 include, for example, a touchscreen, a display, one or more user input components (e.g., a keypad), a speaker, or the like, or any combination thereof. The storage component(s) 908 is a non-volatile memory. In this embodiment, the milling component 910 is a hardware component, such as a lathe, miller, etc. However, the present disclosure is not limited thereto.

Figure 10:
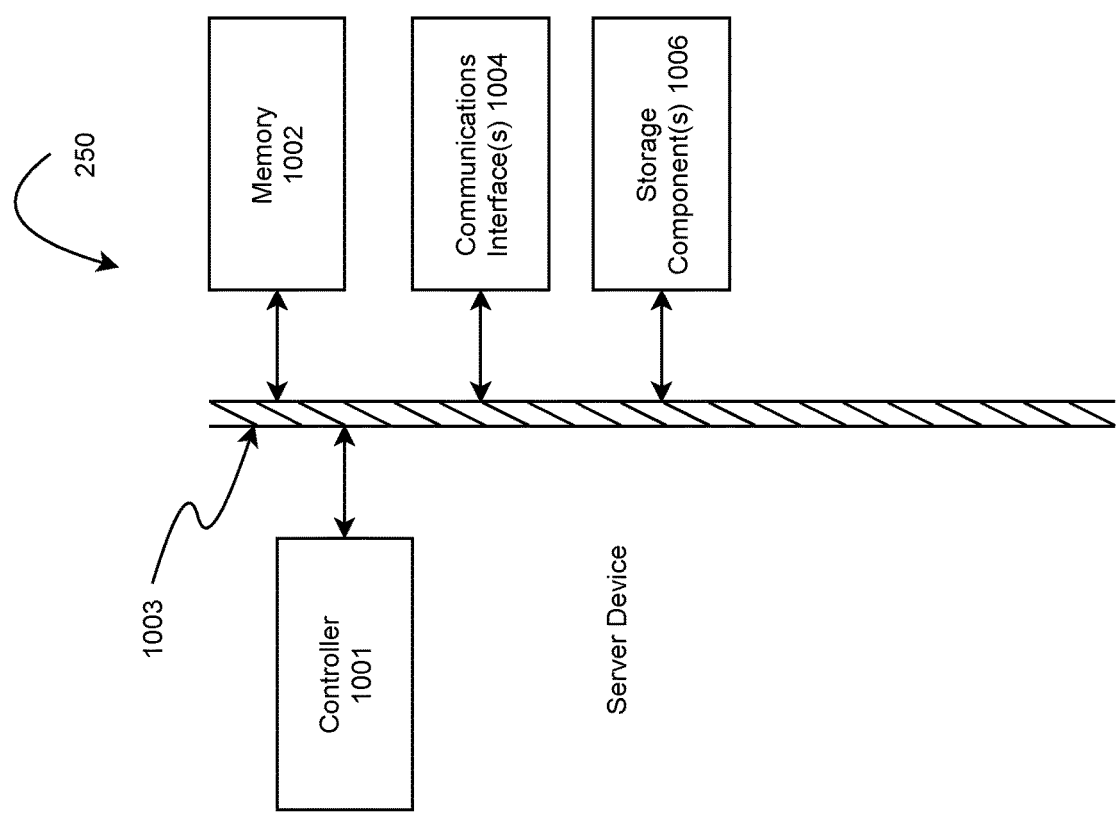
FIG. 10 is a block diagram of a server device 250 according to an embodiment of the present disclosure.

FIG. 10 is a block diagram of a server device 250 according to an embodiment of the present disclosure. As illustrated, server device 250 includes a controller 1001 connected to a memory 1002, one or more secondary storage components 1006, and one or more communications interfaces 1004 by a bus 1003 or similar mechanism. The controller 1001 is a microprocessor, digital Application Specific Integrated Circuit ASIC, Field Programmable Gate Array FPGA, or the like. In general, the server device 250 includes a control system 251 having associated memory 1002. In this embodiment, the controller 1001 is a microprocessor, and the user module 252, inventory module 253, request module 254, and shade match module 255 are implemented in software and stored in the memory 1002 for execution by the controller 1001. However, the present disclosure is not limited thereto. The aforementioned module may be implemented in software, hardware, or a combination thereof. Further, the user registry 256, inventory registry 257, request registry 258, and shade match registry 259 may be stored in the one or more secondary storage components 1006. The secondary storage components 1006 are digital data storage components such as, for example, one or more hard disk drives. The server device 250 also includes a communication interface 1004 enabling the server device 250 to connect to the network 208.

Those skilled in the art will recognize improvements and modifications to the embodiments of the present disclosure. All such improvements and modifications are considered within the scope of the concepts disclosed herein and the claims that follow.

What is claimed is:

1. A shade matching server device comprising:
   one or more processors;
   one or more communications interfaces;
   memory containing instructions executable by the one or more processors with the one or more communications interfaces whereby the server device is operable to:
   receive a stereo lithic file and a shade measurement for a design of a restoration for a target patient from a requesting computing device:
   receive a geographic area designation from the requesting computing device;
   receive inventory information from a plurality of supplying computing devices;
   generate one or more material recommendations for the restoration for the target patient based on inventory information from a plurality of supplying computing devices that match the geographic area designation, wherein the material recommendations comprise recommendations for computer aided design and computer aided manufacturing blocks of different materials;
   receive stereo lithic files and shade measurements for restorations for other patients from supplying computing devices;
   invoke a machine learning process with the stereo lithic file and shade measurement for the restoration for the target patient;
   generate one or more characterization recommendations for the restoration for the target patient based on machine learning and statistical models; and
   send the one or more material recommendations and the one or more characterization recommendations for the restoration for the target patient to the requesting computing device, wherein the one or more characterization recommendations includes one or more staining recommendations and wherein the one or more characterization recommendations include a custom map identifying spatial information for aligning the one or more staining recommendations to the restoration for the target patient after the restoration has been milled from the one or more material recommendations.

2. The server device of claim 1, wherein applying the machine learning process involves applying a translation process to the stereo lithic file for the restoration of the target patient and the stereo lithic files for the restorations for other patients.

3. The server device of claim 1, wherein the one or more characterization recommendations includes one or more glazing recommendations.

4. The server device of claim 1, wherein the one or more characterization recommendations includes information for using the spatial information of the one or more characterization recommendations in an augmented reality application.

5. The server device of claim 1, wherein the server device is further operable to:
   rank order the one or more material recommendations.

6. The server device of claim 1, wherein the server device is further operable to:
   rank order the one or more characterization recommendations.

7. The server device of claim 6, wherein the one or more material recommendations are rank ordered by one of the methods in the group comprising of: the shade of the material that best matches the shade measurement, the cost of the material, the availability of the material, the estimated target delivery time of the material, and the estimated target delivery time of a restoration created from the material.

8. The server device of claim 1, wherein the geographic area designation is one of the group comprising: a physical address, latitude and longitudinal coordinates, what3words, zip code, point and a radius, and an arbitrary polygon.

9. The server device of claim 1, wherein the shade measurement comprises individual measurements for chroma, hue, and value.

10. The server device of claim 1, wherein generating the one or more material recommendations comprises matching the closest values of the individual measurements of chroma, hue, and value for both the shade measurement and the material recommendation.

11. The server device of claim 1, wherein the shade measurement comprises an aggregate measure of chroma, hue, and value.

12. The server device of claim 1, wherein generating the one or more material recommendations comprises matching the closest aggregate measure of chroma, hue, and value for both the shade measurement and the material recommendation.

13. The server device of claim 1, wherein the computer aided design and computer aided manufacturing blocks of different materials are blocks selected from the group of materials comprising: feldspathic porcelain, ceramic resin hybrid, leucite-reinforced porcelain, lithium disilicate, nano ceramic/resin, composite resin, and zirconia reinforced lithium silicate.

14. The server device of claim 1, wherein the server device is further operable to:
   detect a minimum depth error based on the design file and the material recommendation selection; and
   request a reduction coping.

15. The server device of claim 1, wherein the server device is further operable to:
   determine if the design file contains identifying information and request the manufacture of a restoration based on the design file; and
   receive information indicating the completion of the manufacture of the restoration.

16. The server device of claim 1, wherein the server device is further operable to:
   receive information indicating the completion of the reduction coping and wherein the identifying information is one of the group comprising: information identifying a dentist, a dental office, and a patient;

initiate a delivery request with a delivery service, wherein initiating the delivery request comprises at least one of the group consisting of: receiving delivery information to the requesting computing device and sending delivery information to a delivery service; and remove identifying information from the design file.

\* \* \* \* \*